US011692033B2

(12) United States Patent
Billiald et al.

(10) Patent No.: US 11,692,033 B2
(45) Date of Patent: *Jul. 4, 2023

(54) INHIBITION OF PLATELET AGGREGATION USING ANTI-HUMAN GPVI ANTIBODIES

(71) Applicants: ACTICOR BIOTECH, Paris (FR); UNIVERSITÉ PARIS CITÉ, Paris (FR); UNIVERSITÉ PARIS-XIII, Villetaneuse (FR); INSERM (INSTITUT NATIONAL DE LA SANTÉ ET DE LA RECHERCHE MÉDICALE, Paris (FR); UNIVERSITE PARIS-SACLAY, Saint Aubin (FR)

(72) Inventors: Philippe Billiald, Paris (FR); Martine Jandrot-Perrus, Vanves (FR); Gilles Avenard, Montrouge (FR)

(73) Assignees: Acticor Biotech, Paris (FR); Université Paris Cité, Paris (FR); Université Paris-XIII, Villetaneuse (FR); Inserm (Institut National de la Santé et de la Recherche Médicale), Paris (FR); Université Paris-Saclay, Orsay (FR)

( * ) Notice: Subject to any disclaimer, the term of this patent is extended or adjusted under 35 U.S.C. 154(b) by 454 days.

This patent is subject to a terminal disclaimer.

(21) Appl. No.: 16/477,327

(22) PCT Filed: Feb. 2, 2018

(86) PCT No.: PCT/EP2018/052664
§ 371 (c)(1),
(2) Date: Jul. 11, 2019

(87) PCT Pub. No.: WO2018/141909
PCT Pub. Date: Aug. 9, 2018

(65) Prior Publication Data
US 2019/0367608 A1    Dec. 5, 2019

(30) Foreign Application Priority Data
Feb. 3, 2017   (EP) .................................... 17154658

(51) Int. Cl.
*C07K 16/36* (2006.01)
*C07K 16/28* (2006.01)
*A61K 9/00* (2006.01)
*A61K 39/00* (2006.01)

(52) U.S. Cl.
CPC ........ *C07K 16/2803* (2013.01); *A61K 9/0019* (2013.01); *A61K 2039/505* (2013.01); *A61K 2039/54* (2013.01); *A61K 2039/545* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,591,828 A | 1/1997 | Bosslet et al. | |
| 5,892,019 A | 4/1999 | Schlom et al. | |
| 6,245,527 B1* | 6/2001 | Busfield ............... | C07K 14/705 435/243 |
| 6,998,469 B2* | 2/2006 | Tandon ..................... | A61P 7/02 530/389.3 |
| 7,101,549 B2* | 9/2006 | Gill ....................... | C07K 14/705 436/512 |
| 7,977,461 B2 | 7/2011 | Takayama et al. | |
| 8,119,135 B2* | 2/2012 | Munch .................. | G01N 33/86 424/141.1 |
| 9,045,538 B2* | 6/2015 | Jandrot-Perrus .......... | A61P 9/10 |
| 9,045,540 B2* | 6/2015 | Jandrot-Perrus ....... | C07K 16/28 |
| 10,842,870 B2* | 11/2020 | Billiald .................. | C07K 16/28 |
| 2002/0141992 A1 | 10/2002 | Nieswandt | |
| 2003/0186885 A1* | 10/2003 | Tandon ............ | C07K 14/70503 530/388.25 |
| 2004/0001826 A1* | 1/2004 | Gill ...................... | C07K 14/705 424/143.1 |
| 2006/0088531 A1 | 4/2006 | Smethurst et al. | |
| 2007/0071744 A1 | 3/2007 | Munch et al. | |
| 2010/0003244 A1 | 1/2010 | Munch et al. | |

FOREIGN PATENT DOCUMENTS

| | | | |
|---|---|---|---|
| EP | 0352119 A2 | 1/1990 | |
| EP | 0382174 A1 | 8/1990 | |
| EP | 0 404 097 | 12/1990 | |
| EP | 1 224 942 | 7/2002 | |
| EP | 1 228 768 | 8/2002 | |
| EP | 1 538 165 | 6/2005 | |
| EP | 1 876 240 | 1/2008 | |
| EP | 2 363 416 A2 | 9/2011 | |
| WO | WO 1993/001161 | 6/1993 | |
| WO | 9324635 A1 | 12/1993 | |
| WO | WO 2001/000810 | 1/2001 | |
| WO | WO 2003/008454 | 1/2003 | |
| WO | WO 2005/111083 | 11/2005 | |
| WO | WO 2006/118350 | 11/2006 | |
| WO | WO 2006/131512 | 12/2006 | |
| WO | WO 2008/049928 A1 | 5/2008 | |
| WO | WO-2008049928 A1 * | 5/2008 | ............. C07K 16/28 |
| WO | WO 2011/073954 A2 | 6/2011 | |
| WO | 2013034710 A1 | 3/2013 | |

(Continued)

OTHER PUBLICATIONS

Janeway et al., Immunobiology, 3rd edition, 1997 Garland Publishing Inc., pp. 3:1-3:11.*

(Continued)

*Primary Examiner* — Michael Szperka
(74) *Attorney, Agent, or Firm* — Lathrop GPM LLP; James H. Velema; Judith L. Stone-Hulslander

(57) ABSTRACT

The present invention relates to an isolated humanized protein binding to human Glycoprotein VI (hGPVI) for treating a GPVI-related condition in a subject in need thereof, wherein said isolated humanized protein is to be administered during at least 2 hours to the subject, preferably during at least 4 to 6 hours.

20 Claims, 6 Drawing Sheets

Specification includes a Sequence Listing.

(56) References Cited

FOREIGN PATENT DOCUMENTS

| WO | WO 2013/032032 A1 | 3/2013 |
|----|-------------------|--------|
| WO | WO 2017/021539 A2 | 2/2017 |

OTHER PUBLICATIONS

Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368.doi: 10.1038/S41577-019-0126-7.*
Kipriyanov et al., Mol Biotechnol. Jan. 2004;26(1):39-60.*
Bannas et al. "Nanobodies and Nanobody-Based Human Heavy Chain Antibodies as Antitumor Therapeutics", Frontiers in Immunology, Nov. 2017, vol. 8, Article 1603.
Henry et al., "Editorial: single domain antibodies—Biological, Engineering and Emerging Applications", Frontiers in Immunology, Jan. 2018, vol. 9, Article 41.
Pachel et al., "Inhibition of Platelet GPVI Protects Against Myocardial Ischemia-Reperfusion Injury", Arteriosclerosis, Thrombosis, Vascular Biology, Apr. 2016, vol. 36, No. 4, pp. 629-635.
Dütting et al., "Platelet GPVI: a target for antithrombotic therapy?!", Trends in Pharmacological Sciences, Nov. 2012, vol. 33, No. 11, pp. 583-590.
Kraft et al., "Efficacy and Safety of Platelet Glycoprotein Receptor Blockade in Aged and Comorbid Mice With Acute Experimental Stroke", Stroke, Dec. 2015, vol. 46, No. 12, pp. 3502-3506.
Altschul et al. (1990) "Basic local alignment search tool," J. Mol. Biol. 215:403-410.
Burton (1985) "Immunoglobulin G: functional sites," Mol. Immunol. 22(3):161-206.
Carillo et al. (1988) "The Multiple Sequence Alignment Problem in Biology," Siam J. Applied Math. 48(5): 1073-1082.
Caron et al. (1992) "Engineered humanized dimeric forms of IgG are more effective antibodies," J. Exp. Med. 176:1191-1195.
Chothia et al. (1987) "Canonical structures for the hypervariable regions of immunoglobulins," J. Mol. Biol. 196:901-917.
Chothia et al. (1992) "Structural Repertoire of the Human VH Segments," J. Mol. Biol. 227:799-817.
Clackson et al. (1991) "Making antibody fragments using phage display libraries," Nature. 352:624-628.
Delgado et al. (1996) "Enhanced tumour specificity of an anti-carcinoembrionic antigen Fab' fragment by poly(ethylene glycol) (PEG) modification," Br. J. Cancer. 73(2):175-182.
Devereux et al. (1984) "A comprehensive set of sequence analysis programs for the VAX," Nucl. Acid. Res. 12(1 Pt 1):387-95.
Edwards et al., "The Remarkable Flexibility of the Human Antibody Repertoire; Isolation of Over One Thousand Different Antibodies to a Single Protein, BLyS", Journal of Molecular Biology, vol. 334, Issue 1, Nov. 14, 2003, pp. 103-118.
Florian et al., "Anti-GPVI Fab SAR264565 effectively blocks GPVI function in ex vivo human platelets under arterial shear in a perfusion chamber", European Journal of Clinical Pharmacology, vol. 73, No. 8, May 18, 2017, pp. 949-956.
Genbank Database [Online] (Apr. 21, 2005) "platelet glycoprotein VI [Homo sapiens]," Accession No. BAA89353.1. National Center for Biotechnology Information. Accessible on the Internet at URL: https://www.ncbi.nlm.nih.gov/protein/BAA89353.1, 2 pgs. [Last Accessed Apr. 13, 2018].
Goel et al., "Plasticity within the Antigen-Combining Site May Manifest as molecular Mimicry in the Humoral Immune Response", The Journal of Immunology, Dec. 15, 2004 173(12):7358-67.
Graham et al. (1997) "Characteristics of a human cell line transformed by DNA from human adenovirus type 5," J. Gen. Virol. 36(1):59-74.

Holliger et al. (1993) "'Diabodies': Small bivalent and bispecific antibody fragments," Proc. Natl. Acad. Sci. 90:6444-6448.
International Search Report with Written Opinion corresponding to International Patent Application No. PCT/EP2016/068778, dated Jan. 27, 2017.
International Search Report with Written Opinion corresponding to International Patent Application No. PCT/EP2018/052664, dated Mar. 29, 2018 (14 pages).
Jandrot-Perrus et al., "Human platelet glycoprotein VI: Identification of residues involved in the binding to collagen", Blood, The American Society of Hematology, vol. 104, No. 11. Part 1, Nov. 1, 2004, p. 433A.
Janeway et al., Immunobiology: the immune system in health and disease, $3^{rd}$ edition, 1997, Chapters, p. 3:1-3:11, Garland Publishing Inc.
Kanyavuz et al., "Breaking the law: unconventional strategies for antibody diversification", Nature Reviews Immunology 19, Jun. 2019, pp. 355-368 doi: 10.1038/S41577-019-0126-7.
Kohler et al. (1975) "Continuous cultures of fused cells secreting antibody of predefined specificity," Nature. 256:495-497.
Lakhrif et al. (Dec. 18, 2015) "A method to confer Protein L binding ability to any antibody fragment," MAbs. 8(2):379-88.
Lebozec et al., "Design, development and characterization of ACT017, a humanized Fab that blocks platelet's glycoprotein VI function without causing bleeding risks", MABS, vol. 9, No. 6, Jun. 9, 2017, pp. 945-958.
Lefranc et al. (1999) "IMGT, the international ImMunoGeneTics database," Nucleic Acid Res. 27:209-212.
Leong et al. (2001) "Adapting Pharmacokinetic Properties of a Humanized Anti-Interleukin-8 Antibody for Therapeutic Applications Using Site-Specific Pegylation," Cytokines. 16(3):106-119.
Li et al., "The Fab Fragment of a Novel Anti-GPVI Monoclonal Antibody, OM4, Reduces In Vivo Thrombosis Without Bleeding Risk in Rats", Arteriosclerosis, Thrombosis, and Vascular Biol., vol. 27, No. 5, May 1, 2007, pp. 1199-1205.
Llyod et al., "Modelling the human immune response: performance of a 10" human antibody repertoire against a broad panel of therapeutically relevant antigens", Protein Engineering, Design & Selection, vol. 22, No. 3, pp. 159-168 doi: 103 1093/protein/gzn058. Epub Oct. 29, 2008.
Mammadova-Bach et al. (May 14, 2015) "Platelet glycoprotein VI binds to polymerized fibrin and promotes thrombin generation," Blood. 126(5):683-91.
Mangin et al. (2012) "A humanized glycoprotein VI (GPVI) mouse model to assess the antithrombotic efficacies ofanti-GPVI agents," J. Pharmacol. Exp. Ther. 341 (1):156-63.
Marks et al. (1991) "By-passing immunization. Human antibodies from V-gene libraries displayed on phage," J. Mol. Biol. 222:581-597.
Martin et al. (1996) "Structural Families in Loops of Homologous Proteins: Automatic Classification, Modelling and Application to Antibodies," J. Mol. Biol. 263:800-815.
Mather (1980) "Establishment and characterization of two distinct mouse testicular epithelial cell lines," Biol. Reprod. 23:Mather.
Mather et al. (1982) "Culture of testicular cells in hormone-supplemented serum-free medium," Annals N.Y. Acad. Sci. 383:44-68.
Matsumoto et al., "Ex vivo evaluation of anti-GPVI antibody in cynomolgus monkeys: dissociation between anti-platelet aggregatory effect and bleeding time", Thrombosis and Haemostasis, vol. 96, No. 2, Aug. 1, 2006, pp. 167-175.
Morea et al. (2000) "Antibody Modeling: Implications for Engineering and Design," Methods. 20:267-279.
Muzard et al. (2009) "Grafting of protein L-binding activity onto recombinant antibody fragments," Analytical Biochemistry. 388:331-338.
Muzard et al., "Design and humanization of a murine scFv that blocks human platelet glycoprotein VI in vitro" FEBS Journal, vol. 276, No. 15, Aug. 1, 2009, pp. 4207-4222.
O'Connor et al. (2006) "Selective blockade of glycoprotein VI clustering on collagen helices," J. Biol. Chem. 281(44):33505-10.

(56) References Cited

OTHER PUBLICATIONS

Ohlmann et al., "Ex vivo inhibition of thrombus formation by an anti-glycoprotein VI Fab fragment in non-human primates without modification of glycoprotein VI expression", Journal of Thrombosis and Haemostasis, vol. 6, No. 6, Jun. 1, 2008, pp. 1003-1011.
Ono et al. (1999) "The humanized anti-HM1.24 antibody effectively kills multiple myeloma cells by human effector cell-mediated cytotoxicity," Mol. Immunol. 36:387-395.
Pluckthun (1994) "Antibodies from *Escherichia coli*," In; The Pharmacology of Monoclonal Antibodies. vol. 113. Eds.: Rosenburg et al. Springer-Verlag. New York, New York. pp. 269-315.
Posthumus et al. (1990) "Analysis and simulation of a neutralizing epitope of transmissible gastroenteritis virus," J. Virology. 64:3304-3309.
Qu et al. (1999) "Humanization of Immu31, an alpha-fetoprotein-specific antibody," Clin. Cancer Res. 5:3095s-3100s.
Roux et al. (1998) "Comparisons of the ability of human IgG3 hinge mutants, IgM, IgE, and IgA2, to form small immune complexes: a role for flexibility and geometry," J. Immunol. 161:4083-90.
Rudikoff et al., "Single amino acid substitution altering antigen-binding specificity", Proc. Natl. Acad. Sci. USA, Mar. 1982, vol. 79, pp. 1979-1983.
Scatchard et al. (1949) "The attractions of proteins for small molecules and ions," Ann. NY Acad. Sci. 51:660-672.
Shopes (1992) "A genetically engineered human IgG mutant with enhanced cytolytic activity," J. Immunol. 148:2918-2922.
Smethurst et al. (2004) "Identification of the primary collagen-binding surface on human glycoprotein VI by site-directed mutagenesis and by a blocking phage antibody," Blood. 103(3):903-11.
Tomlinson et al. (1995) "The structural repertoire of the human V kappa domain," EMBO J. 14:4628-4638.
Tramontano et al. (1989) "Structural determinants of the conformations of medium-sized loops in proteins," Proteins. 6:382-94.
Tramontano et al. (1990) "Framework residue 71 is a major determinant of the position and conformation of the second hypervariable region in the VH domains of immunoglobulins," J. Mol. Biol. 215:175-182.
Uniprot Database [Online] (First Entered Apr. 4, 2006) "UniProtKB—Q9HCN6 (GPVI_Human)," Accession No. Q9HCN6. UniProt Consortium. Accessible on the Internet at URL: http://www.uniprot.org/uniprot/Q9HCN6, 11 pgs. [Last Accessed Apr. 13, 2018].
Urlaub et al. (1980) "Isolation of Chinese hamster cell mutants deficient in dihydrofolate reductase activity," Proc. Natl. Acad. Sci. USA. 77:4216-4220.
Williams et al. (1996) "Sequence and Evolution of the Human Germline VλRepertoire," J. Mol. Biol. 264:220-232.
Zahid, "Design and Optimization of Recombinant Antibodies Directed Against Platelet Glycoprotein VI with Therapeutic and Diagnostic Potentials Design and Optimization of Recombinant Antibodies Directed Against Platelet Glycoprotein VI with Therapeutic and Diagnostic Potentials. Human health and pathology", Jan. 1, 2014, https://tel.archives-ouvertes.fr/file/index/docid/922980/filename/VA_ZAHID_Muhammad_24112011.pdf.

* cited by examiner

INHIBITION OF PLATELET AGGREGATION USING ANTI-HUMAN GPVI ANTIBODIES

CROSS-REFERENCE TO RELATED APPLICATIONS

This application is a 35 U.S.C. § 371 filing of International Patent Application No. PCT/EP2018/052664, filed Feb. 2, 2018, which claims priority to European Patent Application No. 17154658.3, filed Feb. 3, 2017, the entire disclosures of which are hereby incorporated herein by reference.

FIELD OF INVENTION

The present invention relates to the treatment of cardiovascular diseases. In particular, the present invention relates to a method for treating cardiovascular disease comprising the continuous administration of a novel anti-human glycoprotein VI antibody or fragment thereof to a human patient in need thereof.

BACKGROUND OF INVENTION

Acute coronary and cerebrovascular accidents are currently a major cause of death in the world. In addition, the global incidence of recurrence and death in the 6-month post-treatment period after an acute coronary syndrome is still 8-15%.

In the case of acute coronary syndrome with ST segment elevation, mechanical treatment with coronary angioplasty and introduction of a stent is highly efficient to urgently restore coronary artery flow, but does not prevent morbidity/mortality for about 15% of patients in the next 6 months. Thrombolytic treatments, which are based on long term fibrinolytic, anticoagulant and anti-aggregating drugs associations, give even less encouraging results. Indeed, despite improvements in medical treatment of thrombosis, morbidity/mortality at 6 months is similar to that observed for acute coronary syndrome without ST segment elevation.

Regarding cerebrovascular ischemic accidents, treatments are still very limited due to the generally late caring of most patients and to the hemorrhagic risk of currently available anti-thrombotic treatments.

There is thus still a clinical need for improving treatments for cardiovascular diseases, and especially for new molecules with improved features compared to available molecules and for specific dosage regimens for administering said molecules. The challenge to face is to obtain molecules and protocols of administration with excellent efficiency on the pathological thrombosis but devoid of risk of bleeding.

To answer to this requirement, the target must have a greater role in thrombus formation occurring in a diseased vessel than in physiological hemostasis required to limit the bleeding in a healthy vessel. This is the case of platelet Glycoprotein VI that has been demonstrated in animals to play a role in experimental thrombosis including stroke, vascular remodeling and to be critical in atherothrombosis.

Contrary to αIIbβ3 integrin antagonists, which are currently used in thrombosis treatment and inhibit platelet final activation phase, i.e., platelet aggregation, and to antagonists of platelet recruitment (inhibitors of the P2Y12 ADP receptor and aspirin), GPVI is implicated into several steps of the platelet plug formation: initiation via the interaction with the injured vascular wall, amplification via initial platelet activation leading to the secretion of secondary agonists, the activation of integrins and of platelet procoagulant activity, growth and stabilization via the interaction with fibrin (Mammadova-Bach et al., 2015. Blood. 126(5):683-91). Thus, GPVI antagonists may prevent not only platelet aggregation, but also secondary agonists liberation as well as growth factors and cytokines secretion resulting into vascular lesions development. Finally, GPVI expression is limited to platelets and megakaryocytes, and thus represents a perfectly specific target for anti-thrombosis treatment.

GPVI antagonists were thus developed for treating cardiovascular diseases.

WO 2001/000810 and WO 2003/008454 both describe a soluble GPVI recombinant protein which is a fusion protein between the GPVI extracellular domain and a human Ig Fc domain. This soluble recombinant GPVI protein competes with platelet GPVI for binding collagen. Encouraging results were first obtained with this soluble GPVI protein in a thrombosis murine model, but these results were not confirmed. In addition, this approach involves structural, functional and pharmacological disadvantages. First, this compound is a high molecular weight chimeric protein (~160 kDa). GPVI-Fc targets the collagen exposed at the site of the vascular injury, the amount and accessibility of which are poorly predictable and, thus, the amount of product to be injected constitutes a potential limitation to the use of GPVI-Fc. Another limitation could be the risk of immunization against neoepitopes potentially exposed on the fusion protein.

Neutralizing monoclonal antibodies directed against human GPVI were also described in the art.

For example, EP 1224942 and EP 1228768 disclose the rat monoclonal anti-GPVI antibody JAQ1, which specifically binds to mouse GPVI, for the treatment of thrombotic disease. JAQ1 antibody induces irreversible internalization of the GPVI receptor on mouse platelets.

EP 1538165 describes another rat monoclonal anti-GPVI antibody (hGP 5C4), which Fab fragment was found to have marked inhibitory effects on the main physiological functions of platelets induced by collagen stimulation: stimulation of collagen-mediated physiological activation markers PAC-I and CD62P-Selectin was completely prevented by hGP 5C4 Fab, and hGP 5C4 Fab potently inhibited human platelet aggregation ex vivo without any intrinsic activity. However, 5C4 is a rat antibody, and therefore only presents a very limited therapeutic potential.

WO 2005/111083 describes 4 mouse monoclonal anti-GPVI antibodies OM1, OM2, OM3 and OM4, that were found to inhibit GPVI binding to collagen, collagen-induced secretion and thromboxane A2 (TXA2) formation in vitro, as well as ex vivo collagen-induced platelet aggregation after intravenous injection to Cynomolgus monkeys. OM4 also appears to inhibit thrombus formation in a rat thrombosis model.

WO 2001/000810 also describes various murine monoclonal anti-GPVI antibodies named 8M14.3, 3F8.1, 9E18.3, 3J24.2, 6E12.3, 1P10.2, 4L7.3, 7H4.6, 9O12.2, 7H14.1, and 9E18.2, as well as several human phage antibodies scFv fragments named A9, A10, C9, A4, C10, B4, C3 and D11. Some of these antibodies and scFv fragments were found to inhibit GPVI binding to collagen, including antibodies 9E18.3, 7H4.6, and 9O12.2, and scFv fragments A10, A4, C10, B4, C3 and D11. In addition, 9O12.2 Fab fragments were found to completely block collagen-induced platelet aggregation and secretion, to block fibrin-induced platelet aggregation, to inhibit the procoagulant activity of collagen-stimulated or fibrin-stimulated platelets and platelet adhesion to collagen or fibrin in static conditions, to impair platelet adhesion and to prevent thrombi formation under arterial flow conditions.

WO 2008/049928 describes a scFv fragment derived from 9O12.2, constituted of the VH and VL domains of 9O12.2 monoclonal antibody linked via a (Gly$_4$Ser)$_3$ peptide.

However, none of the currently known anti-GPVI antibodies was shown to be efficient in vivo for preventing and/or treating cardiovascular diseases. In particular, the majority of anti-GPVI antibodies that have been reported appeared not fitted for the development of an antithrombotic for medical use in human, especially due to their animal origin.

In particular, some human phage antibodies scFvs directed to human GPVI have been reported to be inhibitory but their affinity appears to be low. Moreover, cross-linking of GPVI at the platelet surface by a divalent or multivalent ligand such as 9O12.2 whole IgG results in platelet activation via GPVI dimerization and via cross-linking of GPVI to the low affinity Fc receptor (FcγRIIA). In contrast, monovalent 9O12.2 Fab and scFv fragments are inhibitory.

However, these fragments could not be used in therapeutic due to their size and to their animal origin which makes them immunogenic in human patients. Moreover, scFv fragments present a short half-life, which limits their therapeutic potentials.

There is thus still a need for neutralizing GPVI antagonists without immunogenicity in human.

US 2006/0088531 describes a human scFv fragment 10B12, presenting a $K_D$ for binding to human GPVI of about $7.9 \cdot 10^{-7}$ M. Smethurst (Smethurst et al., 2004. *Blood.* 103 (3):903-11) further describes the epitope bound by 10B12 on the Ig-like C2-type domain 1 (D1) of human GPVI. This epitope comprises residues R58, K61, R66, K79 and R80 of human GPVI (numbering based on UniProtKB accession number Q9HCN6).

O'Connor (O'Connor et al., 2006. *J. Biol. Chem.* 281(44): 33505-10) also describes a human scFv fragment 1C3, of low affinity for GPVI (5.4 $10^{-7}$ M), which neither blocked collagen-induced platelet aggregation nor GPVI binding to collagen but which potentiated the inhibitory effect of the 10B12 antibody. The 1C3 epitope in GPVI comprises amino acid 1168, and it is further postulated that this epitope might encompass a region between residues S164 and S182, a region which is highly conserved from mouse to human.

There is thus a need for a humanized antibody (i.e., an antibody without immunogenicity in human) with improved affinity, efficacy and half-life as compared to the antagonists of the prior art, as a means for efficiently and contentedly preventing and/or treating cardiovascular diseases in human. Moreover, these antagonists should preferably be easily purified.

In the art, anti-GPVI antibodies inducing a GPVI depletion phenotype were described (WO 2006/118350, WO 2011/073954, EP 2363416). In particular, WO 2006/118350 discloses an anti-GPVI antibody directed against all mammalians. The epitope of GPVI bound by this antibody is described and corresponds to the loops 9 and 11 of the Ig-like C2-type domain 2 of GPVI, corresponding to amino acid residues 136-142 and 158-162, respectively.

However, GPVI depletion is undesirable since it cannot be controlled, and is irreversible (i.e., it lasts the lifetime of platelets, or even longer due to GPVI depletion on megakaryocytes).

In therapy, a rapid, safe and prolonged (in the range of hours) antiplatelet effect is required. Therefore, antibodies not inducing a GPVI depletion phenotype, and preferably not inducing a decrease in platelet count in vivo (i.e., with a reversible effect) should be developed.

The Applicant developed an antibody anti-GPVI, wherein said antibody or the antigen binding fragment thereof binds to a novel, undescribed, conformational epitope. Said antibody anti-GPVI has a strong affinity for human GPVI, and blocks GPVI interaction with its ligands (including collagen and fibrin), without decreasing the platelet count nor depleting GPVI in vivo. When continuously administered for at least 2 hours, the antibody (or a fragment thereof) demonstrates a prolonged in vivo effect. The present invention thus relates to the therapeutic use of an improved humanized neutralizing antibody specific to human GPVI or a fragment thereof.

SUMMARY

The present invention relates to an isolated humanized protein binding to human Glycoprotein VI (hGPVI) for treating a GPVI-related condition in a subject in need thereof, wherein said isolated humanized protein is to be administered during at least 2 hours to the subject, preferably during at least 4 to 6 hours.

In one embodiment, the isolated humanized protein is injected, preferably by intravenous infusion. In another embodiment, the isolated humanized protein is injected intraperitoneally.

In one embodiment, a dose of humanized protein ranging from about 0.5 mg/kg to about 50 mg/kg, preferably from about 1 mg/kg to about 32 mg/kg, more preferably from about 2.5 mg/kg to about 25 mg/kg, even more preferably from about 5 mg/kg to about 15 mg/kg, and still even more preferably of about 8 mg/kg is to be administered to the patient.

In another embodiment, a dose of the protein for use in the present invention ranges from about 125 mg to about 2000 mg, preferably from about 250 mg to about 1000 mg or from about 500 mg to about 1000 mg.

In one embodiment, a first bolus is administered, wherein preferably said first bolus administration comprises about 10 to 50%, preferably about 20% of the total dosage of the isolated humanized protein to be administered, and wherein preferably said first bolus is administered in about 5 to 30 minutes, preferably in about 15 minutes.

In one embodiment, said protein binds to a conformational epitope comprising:
- at least one amino acid residue from amino acid residues 114 to 142 of hGPVI (SEQ ID NO: 13) or from a sequence sharing at least 60% of identity over amino acid residues 114 to 142 of hGPVI (SEQ ID NO: 13); and
- at least one amino acid residue from amino acid residues 165 to 187 of hGPVI (SEQ ID NO: 13) or from a sequence sharing at least 60% of identity over amino acid residues 165 to 187 of hGPVI (SEQ ID NO: 13).

In one embodiment, said conformational epitope comprises at least one amino acid residue from amino acid residues 121 to 135 of hGPVI (SEQ ID NO: 13) or from a sequence sharing at least 60% of identity over amino acid residues 121 to 135 of hGPVI (SEQ ID NO: 13); and at least one amino acid residue from amino acid residues 169 to 183 of hGPVI (SEQ ID NO: 13) or from a sequence sharing at least 60% of identity over amino acid residues 169 to 183 of hGPVI (SEQ ID NO: 13).

In one embodiment, said conformational epitope comprises at least one amino acid residue from amino acid residues 121 to 136 of hGPVI (SEQ ID NO: 13) or from a sequence sharing at least 60% of identity over amino acid residues 121 to 136 of hGPVI (SEQ ID NO: 13); and at least one amino acid residue from amino acid residues 169 to 183 of hGPVI (SEQ ID NO: 13) or from a sequence sharing at least 60% of identity over amino acid residues 169 to 183 of hGPVI (SEQ ID NO: 13).

In one embodiment, said protein has a $K_D$ for binding to hGPVI less than 15 nM, wherein said $K_D$ is measured by surface plasmon resonance using 960 to 1071 RU of soluble human GPVI and using PBS pH 7.4 as running buffer and wherein said isolated humanized protein does not induce a GPVI depletion phenotype in vivo.

In one embodiment, the isolated humanized protein binding to hGPVI for use according to the present invention is an antibody molecule selected from the group consisting of a whole antibody, a humanized antibody, a single chain antibody, a Fv, a Fab; or an antibody fragment selected from the group consisting of a unibody, a domain antibody, and a nanobody; or a monomeric antibody mimetic selected from the group consisting of an affibody, an affilin, an affitin, an adnectin, an atrimer, an evasin, a DARPin, an anticalin, an avimer, a fynomer, and a versabody, preferably a monovalent antibody.

In one embodiment, the isolated antibody molecule binding to hGPVI is an antibody molecule wherein:
the variable region of the heavy chain comprises at least one of the following CDRs:

```
VH-CDR1:
                                        (SEQ ID NO: 1)
GYTFTSYNM;

VH-CDR2:
                                        (SEQ ID NO: 2)
GIYPGNGDTSYNQKFQG;
and

VH-CDR3:
                                        (SEQ ID NO: 3)
GTVVGDWYFDV;
``` or any CDR having an amino acid sequence that shares at least 60% of identity with SEQ ID NO: 1-3; and
the variable region of the light chain comprises at least one of the following CDRs:

```
VL-CDR1:
                                        (SEQ ID NO: 4)
RSSQSLENSNGNTYLN;

VL-CDR2:
                                        (SEQ ID NO: 5)
RVSNRFS;
and

VL-CDR3:
                                        (SEQ ID NO: 6)
LQLTHVPWT;
``` or any CDR having an amino acid sequence that shares at least 60% of identity with SEQ ID NO: 4-6.

In one embodiment, the variable region of the heavy chain comprises the following CDRs: GYTFTSYNMH (SEQ ID NO: 1), GIYPGNGDTSYNQKFQG (SEQ ID NO: 2) and GTVVGDWYFDV (SEQ ID NO: 3) and the variable region of the light chain comprises the following CDRs: RSSQSLENSNGNTYLN (SEQ ID NO: 4), RVSNRFS (SEQ ID NO: 5) and LQLTHVPWT (SEQ ID NO: 6) or any CDR having an amino acid sequence that shares at least 60% of identity with said SEQ ID NO: 1-6.

In one embodiment, the amino acid sequence encoding the heavy chain variable region is SEQ ID NO: 7 and the amino acid sequence encoding the light variable region is SEQ ID NO: 8, or any sequence having an amino acid sequence that shares at least 60% of identity with said SEQ ID NO: 7 or 8.

In one embodiment, the amino acid sequence encoding the heavy chain variable region is SEQ ID NO: 7 and the amino acid sequence encoding the light variable region is SEQ ID NO: 9, or any sequence having an amino acid sequence that shares at least 60% of identity with said SEQ ID NO: 7 or 9.

In one embodiment, said GPVI-related condition is a cardiovascular disease selected from arterial and venous thrombosis, restenosis, acute coronary syndrome and cerebrovascular accidents due to atherosclerosis.

In one embodiment, said GPVI-related condition is a cardiovascular disease selected from arterial and venous thrombosis, restenosis, acute coronary syndrome, cerebrovascular accidents due to atherosclerosis, myocardial infarction, pulmonary embolism, critical limb ischemia and peripheral artery disease.

DETAILED DESCRIPTION

"Glycoprotein VI (GPVI)" is a platelet membrane glycoprotein that is involved in platelet-collagen interactions. GPVI is a transmembrane collagen receptor expressed on the surface of platelets. In one embodiment, the amino acid sequence of human GPVI is SEQ ID NO: 13 (accession number: BAA89353.1) or any amino acid sequence presenting at least about 90% identity with SEQ ID NO: 13, preferably at least about 91, 92, 93, 94, 95, 96, 97, 98, 99% identity or more with SEQ ID NO: 13.

```
                                       (SEQ ID NO: 13)
MSPSPTALFCLGLCLGRVPA (Signal peptide).

QSGPLPKPSLQALPSSLVPLEKPVTLRCQGPPGVDLYRLEKLSSSRYQDQA

VLFIPAMKRSLAGRYRCSYQNGSLWSLPSDQLELVATGVFAKPSLSAQPGP

AVSSGGDVTLQCQTRYGFDQFALYKEGDPAPYKNPERWYRASFPIITVTAA

HSGTYRCYSFSSRDPYLWSAPSDPLELVVTGTSVTPSRLPTEPPSSVAEFS

EATAELTVSFTNKVFTTETSRSITTSPKESDSPAGPARQYYTKGN (Extracellular domain).

LVRICLGAVILIILAGFLAEDWHSRRKRLRHRGRAVQRPLPPLPPLPQTRK

SHGGQDGGRQDVHSRGLCS (Transmembrane and cytoplasmic domains).
```

The extracellular domain of GPVI is composed of two Ig-like C2-type domains, namely D1 and D2, linked by a hinge interdomain. In one embodiment, D1 comprises amino acid residues 21 to 109 of SEQ ID NO: 13. In one embodiment, the hinge interdomain between D1 and D2 comprises amino acid residues 110 to 113 of SEQ ID NO: 13. In one embodiment, D2 comprises amino acid residues 114 to 207 of SEQ ID NO: 13.

"About" preceding a figure means plus or less 10% of the value of said figure.

"Antibody" or "Immunoglobulin"—As used herein, the term "immunoglobulin" includes a protein having a combination of two heavy and two light chains whether or not it possesses any relevant specific immunoreactivity. "Antibodies" refers to such assemblies which have significant known specific immunoreactive activity to an antigen of interest (e.g. human GPVI). The term "anti-GPVI antibodies" is used herein to refer to antibodies which exhibit immunological specificity for human GPVI protein. As explained elsewhere herein, "specificity" for human GPVI does not exclude cross-reaction with species homologues of GPVI. Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. All five classes of antibodies are within the scope of the present invention; the following discussion will generally be directed to the IgG class of immunoglobulin molecules. With regard to IgG, immunoglobulins comprise two identical light polypeptide chains of molecular weight of about 23,000 Daltons, and two identical heavy chains of molecular weight of about 53,000-70,000 Daltons. The four chains are joined by disulfide bonds in a "Y" configuration wherein the light chains bracket the heavy chains starting at the mouth of the "Y" and continuing through the variable region. The light chains of an antibody are classified as either kappa or lambda ([K], [λ]). Each heavy chain class may be bonded with either a kappa or lambda light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. As indicated above, the variable region of an antibody allows the antibody to selectively recognize and specifically bind epitopes on antigens. That is, the light chain variable domain (VL domain) and heavy chain variable domain (VH domain) of an antibody combine to form the variable region that defines a three-dimensional antigen binding site. This quaternary antibody structure forms the antigen binding site presents at the end of each arm of the "Y". More specifically, the antigen binding site is defined by three complementarity determining regions (CDRs) on each of the VH and VL chains.

"An isolated antibody"—As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non-proteinaceous components. In preferred embodiments, the antibody is purified: (1) to greater than 80, 85, 90, 91, 92, 93, 94, 95% or more by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

"Affinity variants"—As used herein, the term "affinity variant" refers to a variant antibody which exhibits one or more changes in amino acid sequence compared to a reference anti-GPVI antibody, wherein the affinity variant exhibits an altered affinity for the human GPVI protein in comparison to the reference antibody. Typically, affinity variants will exhibit an improved affinity for human GPVI, as compared to the reference anti-GPVI antibody. The improvement may be either a lower $K_D$ for human GPVI, a higher $K_A$ for human GPVI, a faster on-rate for human GPVI or a slower off-rate for human GPVI or an alteration in the pattern of cross-reactivity with non-human GPVI homologues. Affinity variants typically exhibit one or more changes in amino acid sequence (such as, for example in the CDRs), as compared to the reference anti-GPVI antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Binding Site"—As used herein, the term "binding site" comprises a region of a protein which is responsible for selectively binding to a target antigen of interest (e.g. human GPVI). Binding domains or binding regions comprise at least one binding site. Exemplary binding domains include an antibody variable domain. The protein of the invention may comprise a single antigen binding site or multiple (e.g., two, three or four) antigen binding sites. Preferably, however, the protein of the invention comprises a single antigen binding site.

"Conservative amino acid substitution"—As used herein, "conservative amino acid substitutions" are ones in which the amino acid residue is replaced with an amino acid residue that has similar properties, such that one skilled in the art of peptide chemistry would expect the secondary structure and hydropathic nature of the polypeptide to be substantially unchanged. Amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his;

and (5) phe, tyr, trp, his. Other families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

"Chimeric"—As used herein, a "chimeric" protein comprises a first amino acid sequence linked to a second amino acid sequence with which it is not naturally linked in nature. The amino acid sequences may normally exist in separate proteins that are brought together in the fusion protein or they may normally exist in the same protein but are placed in a new arrangement in the fusion protein. A chimeric protein may be created, for example, by chemical synthesis, or by creating and translating a polynucleotide in which the peptide regions are encoded in the desired relationship.

"CDR"—As used herein, the term "CDR" or "complementarity determining region" means the non-contiguous antigen combining sites found within the variable region of both heavy and light chain polypeptides. CDRs were identified according to the following rules as deduced from Kabat (Kabat et al., 1991. *J. Immunol.* 147(5):1709-19) and Chothia & Lesk (Chothia C. and A. M. Lesk, 1987. *J. Mol. Biol.* 196(4):901-17):

CDR-L1:
Start—Approx residue 24;
Residue before is always a Cys;
Residue after is always a Trp. Typically TRP-TYR-GLN, but also, TRP-LEU-GLN, TRP-PHE-GLN, TRP-TYR-LEU;
Length 10 to 17 residues;
CDR-L2:
Start—always 16 residues after the end of L1;
Residues before generally ILE-TYR, but also, VAL-TYR, ILE-LYS, ILE-PHE;
Length always 7 residues;
CDR-L3:
Start—always 33 residues after end of L2;
Residue before is always Cys;
Residues after always PHE-GLY-XXX-GLY (SEQ ID NO: 21);
Length 7 to 11 residues;
CDR-H1:
Start—Approx residue 26 (always 4 after a CYS) [Chothia/AbM definition] Kabat definition starts 5 residues later;
Residues before always CYS-XXX-XXX-XXX (SEQ ID NO: 22);
Residues after always a TRP. Typically TRP-VAL, but also, TRP-ILE, TRP-ALA
Length 10 to 12 residues (AbM definition) Chothia definition excludes the last 4 residues;
CDR-H2:
Start—always 15 residues after the end of Kabat/AbM definition) of CDR-H1 Residues before typically LEU-GLU-TRP-ILE-GLY (SEQ ID NO: 23), but a number of variations;
Residues after LYS/ARG-LEU/ILE/VAL/PHE/THR/ALA-THR/SER/ILE/ALA Length Kabat definition 16 to 19 residues (AbM definition ends 7 residues earlier);
CDR-H3:
Start—always 33 residues after end of CDR-H2 (always 2 after a CYS);
Residues before always CYS-XXX-XXX (typically CYS-ALA-ARG);
Residues after always TRP-GLY-XXX-GLY (SEQ ID NO: 24);
Length 3 to 25 residues.

"CH2 domain"—As used herein, the term "CH2 domain" includes the region of a heavy chain molecule that usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, Molec. Immunol. 22 (1985) 161-206).

"Derived from"—As used herein, the term "derived from" a designated protein (e.g., an anti-GPVI antibody or antigen-binding fragment thereof) refers to the origin of the protein. In an embodiment, the protein or amino acid sequence which is derived from a particular starting protein is a CDR sequence or sequence related thereto. In an embodiment, the amino acid sequence which is derived from a particular starting protein is not contiguous. For example, in an embodiment, one, two, three, four, five, or six CDRs are derived from a starting antibody. In an embodiment, the protein or amino acid sequence which is derived from a particular starting protein or amino acid sequence has an amino acid sequence that is essentially identical to that of the starting sequence, or a region thereof wherein the region consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In an embodiment, the one or more CDR sequences derived from the starting antibody are altered to produce variant CDR sequences, e.g., affinity variants, wherein the variant CDR sequences maintain GPVI binding activity.

"Diabodies"—As used herein, the term "diabodies" refers to small antibody fragments prepared by constructing sFv fragments (see sFv paragraph) with short linkers (about 5-residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 0404097; WO 1993/011161; and Holliger (Holliger et al., 1993. *Proc. Natl. Acad. Sci.* 90(14): 6444-6448).

"Engineered"—As used herein, the term "engineered" includes manipulation of nucleic acid or polypeptide molecules by synthetic means (e.g., by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Epitope"—As used herein, the term "epitope" refers to a specific arrangement of amino acids located on a protein or proteins to which an antibody binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

"Framework region"—As used herein, the term "framework region" or "FR region" includes the amino acid residues that are part of the variable region, but are not part of the CDRs (e.g., using the Kabat/Chothia definition of CDRs). Therefore, a variable region framework is between about 100-120 amino acids in length but includes only those amino acids outside of the CDRs. For the specific example of a heavy chain variable region and for the CDRs as defined by Kabat/Chothia, framework region 1 may correspond to the domain of the variable region encompassing amino acids 1-25; framework region 2 may correspond to the domain of the variable region encompassing amino acids 36-49; framework region 3 may correspond to the domain of the variable region encompassing amino acids 67-98, and framework region 4 may correspond to the domain of the variable region from amino acids 110 to the end of the variable region. The framework regions for the light chain are similarly separated by each of the light chain variable region CDRs. In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainders of the heavy and light variable domains show less inter-molecular variability in amino acid sequence and are termed the framework regions. The framework regions largely adopt a [beta]-sheet conformation and the CDRs form loops which connect, and in some cases form part of, the [beta]-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Fragment"—As used herein, the term "fragment" refers to a part or region of an antibody or antibody chain comprising fewer amino acid residues than an intact or complete antibody or antibody chain. The term "antigen-binding fragment" refers to a protein fragment of an immunoglobulin or antibody that binds antigen or competes with intact antibody (i.e., with the intact antibody from which they were derived) for antigen binding (i.e., specific binding to human GPVI). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')$_2$ fragment, a Fab fragment, an Fd fragment, an Fv fragment, a single domain antibody fragment (DAb), a one-armed (monovalent) antibody, diabodies or any antigen-binding molecule formed by combination, assembly or conjugation of such antigen binding fragments. Fragments can be obtained, e.g., via chemical or enzymatic treatment of an intact or complete antibody or antibody chain or by recombinant means.

The "Fc" fragment of an antibody comprises the carboxy-terminal portions of both H chains held together by disulfides. The effector functions of antibodies are determined by sequences in the Fc region, which region is also the part recognized by Fc receptors (FcR) found on certain types of cells.

"Fv"—As used herein, the term "Fv" is the minimum antibody fragment that contains a complete antigen-recognition and-binding site. This fragment consists of a dimer of one heavy- and one light-chain variable region domain in tight, non-covalent association. From the folding of these two domains emanate six hypervariable loops (three loops each from the H and L chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region"—As used herein, the term "heavy chain region" includes amino acid sequences derived from the constant domains of an immunoglobulin heavy chain. A protein comprising a heavy chain region comprises at least one of: a CH1 domain, a hinge (e.g., upper, middle, and/or lower hinge region) domain, a CH2 domain, a CH3 domain, or a variant or fragment thereof. In an embodiment, a binding molecule of the invention may comprise the Fc region of an immunoglobulin heavy chain (e.g., a hinge portion, a CH2 domain, and a CH3 domain). In another embodiment, a binding molecule of the invention lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain.

In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a protein may comprise a CH2 domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the proteins of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region"—As used herein, the term "hinge region" includes the region of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., 1998. *J Immunol.* 161(8):4083-90).

The terms "hypervariable loop" and "complementarity determining region" are not strictly synonymous, since the hypervariable loops (HVs) are defined on the basis of structure, whereas complementarity determining regions (CDRs) are defined based on sequence variability (Kabat, Elvin A. (1983). *Sequences of proteins of immunological interest* (5th edition). Besthesda, Md.: Public Health Service, National Institutes of Health) and the limits of the HVs and the CDRs may be different in some VH and VL domains. The CDRs of the VL and VH domains can typically be defined by the Kabat/Chothia definition (see above). In one embodiment, the CDRs of the VL and VH domains may comprise the following amino acids: residues 24-39 (CDRL1), 55-61 (CDRL2) and 94-102 (CDRL3) in the light chain variable domain, and residues 26-35 (CDRH1), 50-66 (CDRH2) and 99-109 (CDRH3) in the heavy chain variable domain. Thus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined herein. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., 1992. *J. Mol. Biol.* 227(3):799-817; Tramontano et al., 1990. *J. Mol. Biol.* 215(1):175-182). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"Humanized"—As used herein, the term "humanized" refers to chimeric immunoglobulins, immunoglobulin chains or fragments thereof (such as Fv, Fab, Fab', or other antigen-binding subsequences of antibodies) which contain minimal sequence derived from a murine immunoglobulin. For example, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

"Humanizing substitutions"—As used herein, the term "humanizing substitutions" refers to amino acid substitutions in which the amino acid residue present at a particular position in the VH or VL domain of a non-human anti-GPVI antibody (for example a murine anti-GPVI antibody) is replaced with an amino acid residue which occurs at an equivalent position in a reference human VH or VL domain. The reference human VH or VL domain may be a VH or VL domain encoded by the human germline, in which case the substituted residues may be referred to as "germlining substitutions". Humanizing/germlining substitutions may be made in the framework regions and/or the CDRs of an anti-GPVI antibody, defined herein.

"High human homology"—An antibody comprising a heavy chain variable domain (VH) and a light chain variable domain (VL) will be considered as having high human homology if the VH domains and the VL domains, taken together, exhibit at least 70, 75, 80, 85, 90, 95% or more amino acid sequence identity to the closest matching human germline VH and VL sequences. Antibodies having high human homology may include antibodies comprising VH and VL domains of native non-human antibodies which exhibit sufficiently high % sequence identity human germline sequences, as well as engineered, especially humanized, variants of such antibodies and also "fully human" antibodies. In an embodiment the VH domain of the antibody with high human homology may exhibit an amino acid sequence identity or sequence homology of 75%, 80% or greater with one or more human VH domains across the framework regions FR1, FR2, FR3 and FR4. In other embodiments the amino acid sequence identity or sequence homology between the VH domain of the protein of the invention and the closest matching human germline VH domain sequence may be 85% or greater, 90% or greater, 95% or greater, 97% or greater, or up to 99% or even 100%. In an embodiment the VH domain of the antibody with high human homology may contain one or more (e.g., 1 to 20) amino acid sequence mismatches across the framework regions FR1, FR2, FR3 and FR4, in comparison to the closest matched human VH sequence. In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the protein of the invention and the closest matching human germline VL domain sequence may be 85% or greater 90% or greater, 95% or greater, 97% or greater, or up to 99% or even 100%.

In an embodiment the VL domain of the antibody with high human homology may contain one or more (e.g., 1 to 20, preferably 1 to 10 and more preferably 1 to 5) amino acid sequence mismatches across the framework regions FR1, FR2, FR3 and FR4, in comparison to the closest matched human VL sequence. Before analyzing the percentage sequence identity between the antibody with high human homology and human germline VH and VL, the canonical folds may be determined, which allow the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a data file. In these data files, the key residue positions are shown with the allowed amino acids at each position. The sequence of the variable region of the antibody of interest is given as input and is first aligned with a consensus antibody sequence to assign the Kabat/Chothia numbering scheme. The analysis of the canonical folds uses a set of key residue templates derived by an automated method developed by Martin and Thornton (Martin et al., 1996. *J. Mol. Biol.* 263(5):800-815). With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines). To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions. Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB— excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., Nucleic acid res 27: 209-212 (1999); http://im. gt.cines.fr). Antibodies with high human homology may comprise hypervariable loops or CDRs having human or human-like canonical folds, as discussed in detail below. In an embodiment at least one hypervariable loop or CDR in either the VH domain or the VL domain of the antibody with high human homology may be obtained or derived from a VH or VL domain of a non-human antibody, yet exhibit a predicted or actual canonical fold structure which is substantially identical to a canonical fold structure which occurs in human antibodies. It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al., Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g., X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognized in hypervariable loops of a VH or VL domain of unknown structure; canonical structures can therefore be predicted on the basis of primary amino acid sequence alone. The predicted canonical fold structures for the hypervariable loops of any given VH or VL sequence in an antibody with high human homology can be analyzed using algorithms which are publicly available from www.bioinf.org.uk/abs/chothia.html, www.biochem.ucl.ac.uk/~martin/antibodies.html and www.bioc.unizh.ch/antibody/Sequences/GermlinesNbase_hVk.html. These tools permit query VH or VL sequences to be aligned against human VH or VL domain sequences of known canonical structure, and a prediction of canonical structure made for the hypervariable loops of the query sequence. In the case of the VH domain, H1 and H2 loops may be scored as having a canonical fold structure "substantially identical" to a canonical fold structure known to occur in human antibodies if at least the first, and preferable both, of the following criteria are fulfilled:

1. An identical length, determined by the number of residues, to the closest matching human canonical structural class.

2. At least 33% identity, preferably at least 50% identity with the key amino acid residues described for the corresponding human H1 and H2 canonical structural classes (note for the purposes of the foregoing analysis the H1 and H2 loops are treated separately and each compared against its closest matching human canonical structural class). The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the H1 and H2 loops in the antibody of interest matches the structure of a human canonical fold. Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline. In an embodiment, both HI and H2 in the VH domain of the antibody with high human homology exhibit a predicted or actual canonical fold structure which is substantially identical to a canonical fold structure which occurs in human antibodies. Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, and form one of the following canonical fold combinations: 1-1, 1-2, 1-3, 1-6, 1-4, 2-1, 3-1 and 3-5. An antibody with high human homology may contain a VH domain which exhibits both high sequence identity/sequence homology with human VH, and which contains hypervariable loops exhibiting structural homology with human VH. It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g., antibodies containing VH and VL domains which are derived from camelid conventional antibodies, especially antibodies containing humanized camelid VH and VL domains. Thus, in an embodiment the VH domain of the anti-GPVI antibody with high human homology may exhibit a sequence identity or sequence homology of 70% or greater, 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain, but form a combination of predicted or actual canonical fold structures which is the same as a canonical fold combination known to occur naturally in the same human VH domain. In other embodiments, L1 and L2 in the VL domain of the antibody with high human homology are each obtained from a VL domain of a non-human species, and each exhibits a predicted or actual canonical fold structure which is substantially identical to a canonical fold structure which occurs in human antibodies. As with the VH domains, the hypervariable loops of VL domains of both VLambda and VKappa types can adopt a limited number of conformations or canonical structures, determined in part by length and also by the presence of key amino acid residues at certain canonical positions. Within an antibody of interest having high human homology, L1, L2 and L3 loops obtained from a VL domain of a non-human species, e.g., a Camelidae species, may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.
2. At least 33% identity, preferably at least 50% identity with the key amino acid residues described for the corresponding human L1 or L2 canonical structural classes, from either the VLambda or the VKappa repertoire (note for the purposes of the foregoing analysis the L1 and L2 loops are treated separately and each compared against its closest matching human canonical structural class). The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the loops in the antibody of interest matches a human canonical fold. Key amino acid residues found in the human canonical structural classes for the CDRs of human VLambda and VKappa domains are described by Morea et al., Methods, 20: 267-279 (2000) and Martin et al., J. Mol. Biol., 263:800-815 (1996). The structural repertoire of the human VKappa domain is also described by Tomlinson et al., EMBO J. 14:4628-4638 (1995), and that of the VLambda domain by Williams et al., J. Mol. Biol., 264: 220-232 (1996). The contents of all these documents are to be incorporated herein by reference. L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology may form one of the following canonical fold combinations: 11-7, 13-7(A,B,C), 14-7(A,B), 12-11, 14-11 and 12-12 (as defined in Williams et al., J. Mol. Biol. 264:220-32 (1996) and as shown on http://www.bioc.uzh.ch/antibody/Sequences/GermlinesNBase_hVL.html). In non-limiting embodiments L1 and L2 in the VKappa domain may form one of the following canonical fold combinations: 2-1, 3-1, 4-1 and 6-1 (as defined in Tomlinson et al., EMBO J. 14:4628-38 (1995) and as shown on http://www.bioc.uzh.ch/antibody/Sequences/GermlinesNBase_hVK.html).

In a further embodiment, all three of L1, L2 and L3 in the VL domain of an antibody with high human homology may exhibit a substantially human structure. It is preferred that the VL domain of the antibody with high human homology exhibit both high sequence identity/sequence homology with human VL, and also that the hypervariable loops in the VL domain exhibit structural homology with human VL.

In an embodiment, the VL domain of the anti-GPVI antibody with high human homology may exhibit a sequence identity of 70% or greater, 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain. It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings with maximal sequence and structural homology to human-encoded VH/VL pairings.

"Immunospecific", "specific for" or to "specifically bind"—As used herein, an antibody is said to be "immunospecific", "specific for" or to "specifically bind" an antigen if it reacts at a detectable level with the antigen, preferably with an affinity constant, $K_A$, of greater than or equal to about $10^6$ $M^{-1}$, greater than or equal to about $10^7$ $M^{-1}$, or greater than or equal to $10^8$ $M^{-1}$, or greater than or equal to 1.5 $10^8 M^{-1}$, or greater than or equal to $10^9$ $M^{-1}$ or greater than or equal to 5 $10^9$ $M^{-1}$. Affinity of an antibody for its cognate antigen is also commonly expressed as a dissociation constant $K_D$, and in certain embodiments, an antibody specifically binds to antigen if it binds with a $K_D$ of less than or equal to $10^{-6}$ M, less than or equal to $10^{-7}$ M, or less than or equal to 1.5 $10^{-8}$ M, or less than or equal to $10^{-8}$ M, or less than or equal to 5 $10^{-9}$ M or less than or equal to $10^{-9}$ M. Affinities of antibodies can be readily determined using conventional techniques, for example, those described by Scatchard G et al. (The attractions of proteins for small molecules and ions. *Ann NY Acad Sci* 1949; 51: 660-672). Binding properties of an antibody to antigens, cells or tissues thereof may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, BIAcore).

"Isolated nucleic acid"—As used herein, an "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of less than 100 amino acids. A polypeptide usually refers to a monomeric entity. The term "protein" refers to a sequence of more than 100 amino acids and/or to a multimeric entity. The proteins of the invention are not limited to a specific length of the product.

This term does not refer to or exclude post-expression modifications of the protein, for example, glycosylation, acetylation, phosphorylation and the like, as well as other modifications known in the art, both naturally occurring and non-naturally occurring. A protein may be an entire protein, or a subsequence thereof. Particular proteins of interest in the context of this invention are amino acid subsequences comprising CDRs and being capable of binding an antigen. An "isolated protein" is one that has been identified and separated and/or recovered from a component of its natural environment. In preferred embodiments, the isolated protein will be purified (1) to greater than 80, 85, 90, 95% by weight of protein as determined by the Lowry method, and most preferably more than 96, 97, 98, or 99% by weight, (2) to a degree sufficient to obtain at least residues of N-terminal or internal amino acid sequence by use of a spinning cup sequenator, or (3) to homogeneity by SDS-PAGE under reducing or non-reducing conditions using Coomassie blue or, preferably, silver staining. Isolated protein includes the protein in situ within recombinant cells since at least one component of the protein's natural environment will not be present. Ordinarily, however, isolated protein will be prepared by at least one purification step.

"Identity" or "identical"—As used herein, the term "identity" or "identical", when used in a relationship between the sequences of two or more amino acid sequences, refers to the degree of sequence relatedness between amino acid sequences, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related amino acid sequences can be readily calculated by known methods. Such methods include, but are not limited to, those described in Arthur M. Lesk, *Computational Molecular Biology: Sources and Methods for Sequence Analysis* (New-York: Oxford University Press, 1988); Douglas W. Smith, *Biocomputing: Informatics and Genome Projects* (New-York: Academic Press, 1993); Hugh G. Griffin and Annette M. Griffin, *Computer Analysis of Sequence Data, Part 1* (New Jersey: Humana Press, 1994); Gunnar von Heinje, *Sequence Analysis in Molecular Biology: Treasure Trove or Trivial Pursuit* (Academic Press, 1987); Michael Gribskov and John Devereux, *Sequence Analysis Primer* (New York: M. Stockton Press, 1991); and Carillo et al., 1988. *SIAM J. Appl. Math.* 48(5):1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. *Nucl. Acid. Res.* 12(1 Pt 1):387-395; Genetics Computer Group, University of Wisconsin Biotechnology Center, Madison, Wis.), BLASTP, BLASTN, TBLASTN and FASTA (Altschul et al., 1990. *J. Mol. Biol.* 215(3):403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990. *J. Mol. Biol.* 215(3):403-410). The well-known Smith Waterman algorithm may also be used to determine identity.

"Modified antibody"—As used herein, the term "modified antibody" includes synthetic forms of antibodies which are altered such that they are not naturally occurring, e.g., antibodies that comprise at least two heavy chain regions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain region lacking a CH2 domain and comprising a binding domain of a protein comprising the binding region of one member of a receptor ligand pair.

"Mammal"—As used herein, the term "mammal" refers to any mammal, including humans, domestic and farm animals, and zoo, sports, or pet animals, such as dogs, cats, cattle, horses, sheep, pigs, goats, rabbits, etc. Preferably, the mammal is a primate, more preferably a human.

"Monoclonal antibody"—As used herein, the term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Native sequence"—As used herein, the term "native sequence" nucleotide refers to a polynucleotide that has the same nucleotide sequence as a polynucleotide derived from nature. Accordingly, a "native sequence" protein is one that has the same amino acid sequence as a protein (e.g., antibody) derived from nature (e.g., from any species). Such native sequence polynucleotides and proteins can be isolated from nature or can be produced by recombinant or synthetic means. A polynucleotide "variant", as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences as described herein and evaluating one or more biological activities of the encoded proteins as described herein and/or using any of a number of techniques well known in the art. A protein "variant", as the term is used herein, is a protein that typically differs from a protein specifically disclosed herein in one or more substitutions, deletions, additions and/or insertions. Such variants may be naturally occurring or may be synthetically generated, for example, by modifying one or more of the above protein sequences and evaluating one or more biological activities of the protein as described herein and/or using any of a number of techniques well known in the art. Modifications may be made in the structure of the polynucleotides and proteins of the present invention and still obtain a functional molecule that encodes a variant or derivative protein with desirable characteristics. When it is desired to alter the amino acid sequence of a protein to create an equivalent, or even an improved, variant or region of a protein as described herein, one skilled in the art will typically change one or more of the codons of the encoding DNA sequence. For example, certain amino acids may be substituted for other amino acids in a protein structure without appreciable loss of its ability to bind other proteins (e.g., antigens) or cells. Since it is the binding capacity and nature of a protein that defines that protein's biological functional activity, certain amino acid sequence substitutions can be made in a protein sequence, and of course, its underlying DNA coding sequence, and nevertheless obtain a protein with similar properties. It is thus contemplated that various changes may be made in the amino acid sequences of the disclosed compositions, or corresponding DNA sequences that encode said proteins without appreciable loss of their biological utility or activity. In many instances, a protein variant will contain one or more conservative substitutions. A "conservative substitution" is one in which an amino acid is substituted for another amino acid that has similar properties, such that one skilled in the art of peptide chemistry would expect the secondary structure and hydropathic nature of the protein to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take several of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant proteins differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the protein.

"Pharmaceutically acceptable excipient"—As used herein, the term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by regulatory offices, such as, for example, FDA Office or EMA.

"Specificity"—As used herein, the term "specificity" refers to the ability to specifically bind (e.g., immunoreact with) a given target, e.g., GPVI. A protein may be monospecific and contain one or more binding sites which specifically bind a target, or a protein may be multispecific and contain two or more binding sites which specifically bind the same or different targets. In an embodiment, an antibody as described herein is specific for more than one target. For example, in an embodiment, a multispecific binding molecule binds to GPVI and a second molecule.

"Single-chain Fv" also abbreviated as "sFv" or "scFv"— As used herein, the terms "Single-chain Fv", "sFv" or "scFv" are antibody fragments that comprise the VH and VL antibody domains connected into a single amino acid chain.

Preferably, the sFv amino acid sequence further comprises a peptidic linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

"Subject"—As used herein, the term "subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease.

"Synthetic"—As used herein, the term "synthetic" with respect to proteins includes proteins which comprise an amino acid sequence that is not naturally occurring. For example, non-naturally occurring proteins are modified forms of naturally occurring proteins (e.g., comprising a mutation such as an addition, substitution or deletion) or proteins which comprise a first amino acid sequence (which may or may not be naturally occurring) that is linked in a linear sequence of amino acids to a second amino acid sequence (which may or may not be naturally occurring) to which it is not naturally linked in nature.

"Therapeutically effective amount" means level or amount of agent that is aimed at, without causing significant negative or adverse side effects to the target, (1) delaying or preventing the onset of GPVI-related disease; (2) slowing down or stopping the progression, aggravation, or deterioration of one or more symptoms of the GPVI-related disease; (3) bringing about ameliorations of the symptoms of the GPVI-related disease; (4) reducing the severity or incidence of the GPVI-related disease; or (5) curing the GPVI-related disease. A therapeutically effective amount may be administered prior to the onset of the GPVI-related disease, for a prophylactic or preventive action. Alternatively or additionally, the therapeutically effective amount may be administered after initiation of the GPVI-related disease, for a therapeutic action.

"Treating" or "treatment" or "alleviation"—As used herein, the terms "treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic condition or disorder if, after receiving a therapeutic amount of a protein according to the present invention, the subject or mammal shows observable and/or measurable improvement in one or more of the following: reduction in the number of pathogenic cells; reduction in the percent of total cells that are pathogenic; and/or relief to some extent, of one or more of the symptoms associated with the specific disease or condition; reduced morbidity and mortality, and/or improvement in quality of life issues. The above parameters for assessing successful treatment and improvement in the disease are readily measurable by routine procedures familiar to a physician.

"Variable region" or "variable domain"—As used herein, the term "variable" refers to the fact that certain regions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1 ($\lambda$), L2 ($\lambda$) and L3 ($\lambda$) and may be defined as comprising residues 24-33 (L1($\lambda$), consisting of 9, 10 or 11 amino acid residues), 49-53 L2 ($\lambda$), consisting of 3 residues) and 90-96 (L3($\lambda$), consisting of 6 residues) in the VL domain (Morea et al., Methods 20:267-279 (2000)). The first, second and third hypervariable loops of the VKappa light chain domain are referred to herein as L1($\kappa$), L2($\kappa$) and L3($\kappa$) and may be defined as comprising residues 25-33 (L1($\kappa$), consisting of 6, 7, 8, 11, 12 or 13 residues), 49-53 (L2($\kappa$), consisting of 3 residues) and 90-97 (L3($\kappa$), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (HI, consisting of 7, 8 or 9 residues), 52-56 (H2, consisting of 3 or 4 residues) and 91-105 (H3, highly variable in length) in the VH domain (Morea et al., Methods 20:267-279 (2000)). Unless otherwise indicated, the terms L1, L2 and L3 respectively refer to the first, second and third hypervariable loops of a VL domain, and encompass hypervariable loops obtained from both VKappa and VLambda isotypes. The terms H1, H2 and H3 respectively refer to the first, second and third hypervariable loops of the VH domain, and encompass hypervariable loops obtained from any of the known heavy chain isotypes, including [gamma], [epsilon], [delta], [alpha] or [mu]. The hypervariable loops L1, L2, L3, H1, H2 and H3 may each comprise part of a "complementarity determining region" or "CDR", as defined hereinabove.

"Valency"—As used herein, the term "valency" refers to the number of potential target binding sites in a protein. Each target binding site specifically binds one target molecule or specific site on a target molecule. When a protein comprises more than one target binding site, each target binding site may specifically bind the same or different molecules (e.g., may bind to different ligands or different antigens, or different epitopes on the same antigen). The subject binding molecules preferably have at least one binding site specific for a human GPVI molecule. Preferably, the proteins provided herein are monovalent.

An object of the present invention is an isolated humanized protein binding to human Glycoprotein VI (hGPVI) for treating or for use in treating a GPVI-related condition in a subject in need thereof, wherein said isolated humanized protein is administered (or is to be administered) during at least 2 hours to the subject, preferably during at least 4 to 6 hours.

In one embodiment, the isolated humanized proteins binding to human GPVI are isolated humanized antibodies against human GPVI.

In one embodiment, the isolated protein is purified.

In one embodiment, the protein binds to the extracellular domain of GPVI.

In one embodiment, the protein binds to the Ig-like C2-type domain 2 (D2) of human GPVI.

Thus, in one embodiment, the protein binds to an epitope comprising at least one amino acid residue from amino acid residues 114 to 207 of human GPVI (SEQ ID NO: 13) or from a sequence sharing at least 60%, 70%, 75%, 80%, 90%, 95%, 96%, 97%, 98%, 99% of identity over amino acid residues 114 to 207 of human GPVI (SEQ ID NO: 13).

In one embodiment, said epitope comprises at least one amino acid residue from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acid residues from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, the epitope comprises at least one (e.g., 1, 2, 3, 4, 5, 6, 7, or 8) of the following residues in GPVI sequence (SEQ ID NO: 13): 125S, 126S, 128G, 133Q, 136T, 171T, 172A and/or 174H. In one embodiment, the epitope comprises at least one (e.g., 1, 2, 3, 4, 5, 6, or 7) of the following residues in GPVI sequence (SEQ ID NO: 13): 125S, 126S, 128G, 133Q, 171T, 172A and/or 174H.

In one embodiment, said epitope comprises at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28 amino acid residues from 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13).

In one embodiment, said epitope comprises at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21 amino acid residues from 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13).

In one embodiment, the epitope comprises at least one (e.g., 1, 2, 3, 4, or 5) of the following residues in GPVI sequence (SEQ ID NO: 13): 125S, 126S, 128G, 133Q, and/or 136T. In one embodiment, the epitope comprises at least one (e.g., 1, 2, 3, or 4) of the following residues in GPVI sequence (SEQ ID NO: 13): 125S, 126S, 128G, and/or 133Q.

In one embodiment, said epitope comprises at least one amino acid residue from amino acid residues 165 to 187, preferably from 166 to 186, more preferably from 167 to 185, more preferably from 168 to 184, even more preferably from 169 to 183 of human GPVI (SEQ ID NO: 13), or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said epitope comprises at least 1, 2, 3, 4, 5, 6, 7, 8, 9, 10, 11, 12, 13, 14, 15, 16, 17, 18, 19, 20, 21, 22 amino acid residues from 165 to 187, preferably from 166 to 186, more preferably from 167 to 185, more preferably from 168 to 184, even more preferably from 169 to 183 of human GPVI (SEQ ID NO: 13), or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, the epitope comprises at least one (e.g. 1, 2 or 3) of the following residues in GPVI sequence: 171T, 172A and/or 174H.

In one embodiment, the isolated protein binds to a conformational epitope.

In one embodiment, said conformational epitope comprises at least one, preferably at least two, amino acid residue(s) of human GPVI.

In one embodiment, said conformational epitope comprises at least one, preferably at least two, amino acid residue(s) of the Ig-like C2-type domain 2 (D2) of human GPVI.

In one embodiment, said conformational epitope comprises at least one, preferably at least two, amino acid residue(s) from 114 to 207 of human GPVI (SEQ ID NO: 13).

In one embodiment, said conformational epitope comprises at least one amino acid residue from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acid residues from amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13), or from a sequence sharing at least 60%, 70%, 75%, 80%, 90%, 95%, 96%, 97%, 98%, 99% of identity over amino acid residues 114 to 187, preferably from 115 to 187, more preferably from 116 to 187, more preferably from 117 to 187, more preferably from 118 to 186, more preferably from 119 to 185, more preferably from 120 to 184, even more preferably from 121 to 183 of human GPVI (SEQ ID NO: 13).

In one embodiment, the conformational epitope comprises at least one (e.g., 1, 2, 3, 4, 5, 6, 7, or 8) of the following residues in GPVI sequence (SEQ ID NO: 13): 125S, 126S, 128G, 133Q, 136T, 171T, 172A and/or 174H. In one embodiment, the conformational epitope comprises at least one (e.g., 1, 2, 3, 4, 5, 6, or 7) of the following residues in GPVI sequence (SEQ ID NO: 13): 125S, 126S, 128G, 133Q, 171T, 172A and/or 174H.

In one embodiment, said conformational epitope comprises at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22, 23, 24, 25, 26, 27, 28 amino acid residues from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13).

In one embodiment, said conformational epitope comprises at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21 amino acid residues from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13), or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13).

In one embodiment, the conformational epitope comprises at least one (e.g., 1, 2, 3, 4, or 5) of the following residues in GPVI sequence (SEQ ID NO: 13): 125S, 126S, 128G, 133Q, and/or 136T. In one embodiment, the conformational epitope comprises at least one (e.g., 1, 2, 3, or 4) of the following residues in GPVI sequence (SEQ ID NO: 13): 125S, 126S, 128G, and/or 133Q.

In one embodiment, said conformational epitope comprises at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, the conformational epitope comprises at least one (e.g. 1, 2 or 3) of the following residues in GPVI sequence: 171T, 172A and/or 174H.

In one embodiment, said conformational epitope comprises:
- at least one amino acid residue from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13); and
- at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least 1, 2, 3, 4, 5, 6, 7, 8, 9, 10, 11, 12, 13, 14, 15, 16, 17, 18, 19, 20, 21, 22, 23, 24, 25, 26, 27, 28 amino acid residues from amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 114 to 142, preferably from 115 to 141, more preferably from 116 to 140, more preferably from 117 to 139, more preferably from 118 to 138, more preferably from 119 to 137, more preferably from 120 to 136, even more preferably from 121 to 135 or from 121 to 136 of human GPVI (SEQ ID NO: 13); and
- at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least one amino acid residue from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13); and
- at least one amino acid residue from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises:
- at least 1, 2, 3, 4, 5, 6, 7, 8, 9, 10, 11, 12, 13, 14, 15, 16, 17, 18, 19, 20, 21 amino acid residues from amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 114 to 135, preferably from 115 to 135, more preferably from 116 to 135, more preferably from 117 to 135, more preferably from 118 to 135, more preferably from 119 to 135, more preferably from 120 to 135, even more preferably from 121 to 135 or from 121 to 136 of human GPVI (SEQ ID NO: 13); and
- at least 1, 2, 3, 4, 5, 6, 7, 8, 9, 10, 11, 12, 13, 14, 15, 16, 17, 18, 19, 20, 21, 22 amino acid residues from amino acid residues 165 to 187, preferably from 166 to 186, more preferably from 167 to 185, more preferably from 168 to 184, even more preferably from 169 to 183 of human GPVI (SEQ ID NO: 13) or from a sequence sharing at least 60%, 70%, 75%, 80%, 90%, 95%, 96%, 97%, 98%, 99% of identity over amino acid residues 165 to 187, preferably from 166 to 186, more preferably from 167 to 185, more preferably from 168 to 184, even more preferably from 169 to 183 of human GPVI (SEQ ID NO: 13).

In one embodiment, said conformational epitope comprises at least one amino acid residue from amino acid residues 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and at least one amino acid residue from amino acid residues 169 to 183 of human GPVI (SEQ ID NO: 13) or from a sequence sharing at least 60%, 70%, 75%, 80%, 90%, 95%, 96%, 97%, 98%, 99% of identity over amino acid residues 169 to 183 of human GPVI (SEQ ID NO: 13).

Thus, in one embodiment, the protein binds to a conformational epitope comprising at least one amino acid residue from amino acid residues 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and at least one amino acid residue from amino acid residues 169 to 183 of human GPVI (SEQ ID NO: 13) or from a sequence sharing at least 60%, 70%, 75%, 80%, 90%, 95%, 96%, 97%, 98%, 99% of identity over amino acid residues 169 to 183 of human GPVI (SEQ ID NO: 13).

In one embodiment, said conformational epitope comprises at least one amino acid residue from amino acid residues 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and at least one amino acid residue from amino acid residues 169 to 180 of human GPVI (SEQ ID NO: 13) or from a sequence sharing at least 60%, 70%, 75%, 80%, 90%, 95%, 96%, 97%, 98%, 99% of identity over amino acid residues 169 to 180 of human GPVI (SEQ ID NO: 13).

Thus, in one embodiment, the protein binds to a conformational epitope comprising at least one amino acid residue from amino acid residues 121 to 135 or from 121 to 136 of human GPVI (SEQ ID NO: 13) or from a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and at least one amino acid residue from amino acid residues 169 to 180 of human GPVI (SEQ ID NO: 13) or from a sequence sharing at least 60%, 70%, 75%, 80%, 90%, 95%, 96%, 97%, 98%, 99% of identity over amino acid residues 169 to 180 of human GPVI (SEQ ID NO: 13).

In one embodiment, the conformational epitope comprises:
- at least one (e.g., 1, 2, 3, 4, or 5) of the following residues in GPVI sequence (SEQ ID NO: 13): 125S, 126S, 128G, 133Q, and/or 136T; and
- at least one (e.g., 1, 2 or 3) of the following residues in GPVI sequence (SEQ ID NO: 13):171T, 172A and/or 174H.

In one embodiment, the conformational epitope comprises:
- at least one (e.g., 1, 2, 3, or 4) of the following residues in GPVI sequence (SEQ ID NO: 13): 125S, 126S, 128G, and/or 133Q; and
- at least one (e.g., 1, 2 or 3) of the following residues in GPVI sequence (SEQ ID NO: 13):171T, 172A and/or 174H.

In one embodiment, the conformational epitope comprises:
- the following residues in GPVI sequence (SEQ ID NO: 13): 125S, 126S, 128G, 133Q, and 136T; and
- the following residues in GPVI sequence (SEQ ID NO: 13):171T, 172A and 174H.

In one embodiment, the conformational epitope comprises:
- the following residues in GPVI sequence (SEQ ID NO: 13): 125S, 126S, 128G, and 133Q; and
- the following residues in GPVI sequence (SEQ ID NO: 13):171T, 172A and 174H.

In one embodiment, said conformational epitope consists of:
- amino acid residues 121 to 135 or from 121 to 136 of human GPVI (SEQ ID NO: 13) or a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and
- amino acid residues 169 to 183 of human GPVI (SEQ ID NO: 13) or a sequence sharing at least 60%, 70%, 75%, 80%, 90%, 95%, 96%, 97%, 98%, 99% of identity over amino acid residues 169 to 183 of human GPVI (SEQ ID NO: 13).

Thus, in one embodiment, the protein binds to a conformational epitope consisting of:
- amino acid residues 121 to 135 or from 121 to 136 of human GPVI (SEQ ID NO: 13) or a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and
- amino acid residues 169 to 183 of human GPVI (SEQ ID NO: 13) or a sequence sharing at least 60%, 70%, 75%, 80%, 90%, 95%, 96%, 97%, 98%, 99% of identity over amino acid residues 169 to 183 of human GPVI (SEQ ID NO: 13).

In one embodiment, said conformational epitope consists of:
- amino acid residues 121 to 135 or from 121 to 136 of human GPVI (SEQ ID NO: 13) or a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and
- amino acid residues 169 to 180 of human GPVI (SEQ ID NO: 13) or a sequence sharing at least 60%, 70%, 75%, 80%, 90%, 95%, 96%, 97%, 98%, 99% of identity over amino acid residues 169 to 180 of human GPVI (SEQ ID NO: 13).

Thus, in one embodiment, the protein binds to a conformational epitope consisting of:
- amino acid residues 121 to 135 or from 121 to 136 of human GPVI (SEQ ID NO: 13) or a sequence sharing at least 60%, 70%, 75%, 80%, 90%, 95%, 96%, 97%, 98%, 99% of identity over amino acid residues 121 to 135 or from 121 to 136 of human GPVI (SEQ ID NO: 13); and
- amino acid residues 169 to 180 of human GPVI (SEQ ID NO: 13) or a sequence sharing at least 60%, 70%, 75%, 80%, 90%, 95%, 96%, 97%, 98%, 99% of identity over amino acid residues 169 to 180 of human GPVI (SEQ ID NO: 13).

In one embodiment, the isolated protein binding to human GPVI for use in the present invention has a $K_D$ for binding to human GPVI, preferably soluble human GPVI, less than or equal to 15 nM, preferably less than or equal to 10 nM and more preferably less than or equal to 5 nM.

In one embodiment, the isolated protein has a $k_{off}$ for binding to human GPVI of less than or equal to about $8 \cdot 10^{-4}$ sec$^{-1}$, preferably less than or equal to about $6 \cdot 10^{-4}$ sec$^{-1}$, and more preferably less than or equal to about $4 \cdot 10^{-4}$ sec$^{-1}$.

In one embodiment, the isolated protein has a $k_{on}$ for binding to human GPVI of at least about $5\times10^4$ $M^{-1}$ $sec^{-1}$, preferably at least about $5.5\times10^4$ $M^{-1}$ $sec^{-1}$, and more preferably at least about $5.9\times10^4$ $M^{-1}$ $sec^{-1}$ and more preferably at least about $6\times10^{-4}$ $sec^{-1}$.

In one embodiment, the $K_D$ may be determined by Surface plasmon resonance (SPR, BIAcore), using immobilized soluble GPVI at a dose ranging from about 700 to about 1600 resonance units (RU) (corresponding to about 8.5 to about 11.3 fmol/mm$^2$), preferably from about 850 to about 1200 RU, more preferably from about 950 to about 1075 RU and/or using PBS pH 7.4 as running buffer, and/or using BIAevaluation version 3.0 software for analyzing data. In one embodiment, soluble GPVI corresponds to the extracellular domain of GPVI fused at its C-terminus via a linker (such as, for example, via a Gly-Gly-Arg linker) to a hFc sequence. This soluble GPVI may be referred to as soluble GPVI-Fc.

Methods for determining the affinity of a protein for a ligand are well known in the art. An example of a method for determining the affinity of a protein for soluble GPVI is shown below:

Binding of the protein to soluble human GPVI is analyzed with surface plasmon resonance using a BIAcore 2000 system (Uppsala, Sweden).

Soluble GPVI-Fc is immobilized at a dose ranging from about 700 to about 1600 RU (corresponding to about 8.5 to about 11.3 fmol/mm$^2$), preferably from about 850 to about 1200 RU, more preferably from about 950 to about 1075 RU, and even more preferably from about 960 to about 1071 RU onto a Carboxy-Methyl Dextran CMS sensor chip using the amine coupling method (Wizard procedure). The protein is then passed over the immobilized GPVI-Fc in PBS pH 7.4 (10 mM phosphate, 138 mM NaCl, 2.7 mM KCl, pH 7.42 at 25.4° C.) at a flow rate of 20 µL/min at 25° C. Kinetic constants ($k_{on}$, $k_{off}$) and affinity are determined using BIAevaluation version 3.0 software, by fitting data to binding model. PBS pH 7.4 is the running buffer.

In an embodiment, the protein for use in the present invention is an antibody molecule or a fragment thereof selected from the group consisting of a whole antibody, a humanized antibody, a single chain antibody, a dimeric single chain antibody, a Fv, a Fab, a F(ab)'$_2$, a defucosylated antibody, a bi-specific antibody, a diabody, a triabody and a tetrabody.

In another embodiment, the protein for use in the present invention is an antibody fragment selected from the group consisting of a unibody, a domain antibody, and a nanobody.

In another embodiment, the protein for use in the present invention is an antibody mimetic selected from the group consisting of an affibody, an affilin, an affitin, an adnectin, an atrimer, an evasin, a DARPin, an anticalin, an avimer, a fynomer, a versabody and a duocalin.

A domain antibody is well known in the art and refers to the smallest functional binding units of antibodies, corresponding to the variable regions of either the heavy or light chains of antibodies.

A nanobody is well known in the art and refers to an antibody-derived therapeutic protein that contains the unique structural and functional properties of naturally-occurring heavy chain antibodies. These heavy chain antibodies may contain a single variable domain (VHH) and two constant domains (CH2 and CH3).

A unibody is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

An affibody is well known in the art and refers to affinity proteins based on a 58 amino acid residue protein domain, derived from one of the IgG binding domain of staphylococcal protein A.

DARPins (Designed Ankyrin Repeat Proteins) are well known in the art and refer to an antibody mimetic DRP (designed repeat protein) technology developed to exploit the binding abilities of non-antibody proteins.

Anticalins are well known in the art and refer to another antibody mimetic technology, wherein the binding specificity is derived from lipocalins. Anticalins may also be formatted as dual targeting protein, called Duocalins.

Avimers are well known in the art and refer to another antibody mimetic technology.

Versabodies are well known in the art and refer to another antibody mimetic technology. They are small proteins of 3-5 kDa with >15% cysteines, which form a high disulfide density scaffold, replacing the hydrophobic core the typical proteins have.

In one embodiment, the protein for use in the present invention is monovalent, and is preferably selected from a whole monovalent antibody, a humanized monovalent antibody, a single chain antibody, a Fv, a Fab, or an antibody fragment selected from the group consisting of a unibody, a domain antibody, and a nanobody; or a monomeric antibody mimetic selected from the group consisting of an affibody, an affilin, an affitin, an adnectin, an atrimer, an evasin, a DARPin, an anticalin, an avimer, a fynomer, and a versabody.

In another embodiment, the protein for use in the present invention is an immunoconjugate comprising an antibody or fragment thereof conjugated to a therapeutic agent.

In another embodiment, the protein for use in the present invention is a conjugate comprising a protein conjugated to an imaging agent. Said protein could be used for example for imaging applications.

In an embodiment, the protein for use in the present invention is a monoclonal antibody or a fragment thereof.

In another embodiment, the protein for use in the present invention is a polyclonal antibody or a fragment thereof.

Another object of the invention is thus an anti-hGPVI antibody or antigen binding fragment thereof for treating, or for use in treating, a GPVI-related condition in a subject in need thereof, wherein said anti-hGPVI antibody or antigen binding fragment thereof is administered (or is to be administered) during at least 2 hours to the subject, preferably during at least 4 to 6 hours.

In one embodiment, the variable region of the heavy chain of the anti-hGPVI antibody or antigen binding fragment thereof for use in the present invention comprises at least one of the followings CDRs:

VH-CDR1:
(SEQ ID NO: 1)
GYTFTSYNM;

VH-CDR2:
(SEQ ID NO: 2)
GIYPGNGDTSYNQKFQG;
and

VH-CDR3:
(SEQ ID NO: 3)
GTVVGDWYFDV.

CDR numbering and definition are according to the Kabat/Chothia definition.

In one embodiment, the variable region of the light chain of the anti-hGPVI antibody or antigen binding fragment thereof for use in the present invention comprises at least one of the followings CDRs:

```
VL-CDR1:
                                    (SEQ ID NO: 4)
RSSQSLENSNGNTYLN;

VL-CDR2:
                                    (SEQ ID NO: 5)
RVSNRFS;
and

VL-CDR3:
                                    (SEQ ID NO: 6)
LQLTHVPWT.
```

CDR numbering and definition are according to the Kabat/Chothia definition.

In one embodiment, the anti-hGPVI antibody or antigen binding fragment thereof for use in the present invention comprises:
  in the heavy chain, at least one of the following CDR: GYTFTSYNMH (SEQ ID NO: 1), GIYPGNGDT-SYNQKFQG (SEQ ID NO: 2) and GTVVGDWYFDV (SEQ ID NO: 3); and/or
  in the light chain, at least one of the following CDR: RSSQSLENSNGNTYLN (SEQ ID NO: 4), RVSNRFS (SEQ ID NO: 5), and LQLTHVPWT (SEQ ID NO: 6).

In another embodiment of the invention, the anti-hGPVI antibody or antigen binding fragment thereof for use in the present invention comprises in its heavy chain the 3 CDRs SEQ ID NO: 1, SEQ ID NO: 2 and SEQ ID NO: 3.

In another embodiment of the invention, the anti-hGPVI antibody or antigen binding fragment thereof for use in the present invention comprises in its light chain the 3 CDRs SEQ ID NO: 4, SEQ ID NO: 5 and SEQ ID NO: 6.

In another embodiment of the invention, the anti-hGPVI antibody or antigen binding fragment thereof for use in the present invention comprises in its heavy chain the 3 CDRs SEQ ID NO: 1, SEQ ID NO: 2 and SEQ ID NO: 3, and in its light chain the 3 CDRs SEQ ID NO: 4, SEQ ID NO: 5 and SEQ ID NO: 6.

In another embodiment of the invention, the anti-hGPVI antibody or antigen binding fragment thereof for use in the present invention comprises in its heavy chain the 3 CDRs SEQ ID NO: 1, SEQ ID NO: 2 and SEQ ID NO: 3, and in its light chain the 3 CDRs SEQ ID NO: 4, SEQ ID NO: 5 and SEQ ID NO: 6, optionally wherein one, two, three or more of the amino acids in any of said sequences may be substituted by a different amino acid.

According to the invention, any of the CDRs 1, 2 and 3 of the heavy and light chains may be characterized as having an amino acid sequence that shares at least 60%, 70%, 75%, 80%, 90%, 95%, 96%, 97%, 98%, 99% of identity with the particular CDR or sets of CDRs listed in the corresponding SEQ ID NO.

In another embodiment of the invention, the anti-hGPVI antibody or antigen binding fragment thereof for use in the present invention is an antibody having:
  (i) the heavy chain CDR 1, 2 and 3 (VH-CDR1, VH-CDR2, VH-CDR3) amino acid sequences as shown in SEQ ID NO: 1, 2 and 3 respectively; and
  (ii) the light chain CDR 1, 2 and 3 (VL-CDR1, VL-CDR2, VL-CDR3) amino acid sequences as shown in SEQ ID NO: 4, 5 and 6 respectively;

optionally wherein one, two, three or more of the amino acids in any of said sequences may be substituted by a different amino acid.

In one embodiment, the anti-GPVI antibody or antigen binding fragment thereof for use in the present invention comprises a heavy chain variable region comprising or consisting of the sequence SEQ ID NO: 7.

```
                                    (SEQ ID NO: 7)
QVQLVQSGAEVKKPGASVKVSCKASGYTFTSYNMHWVRQAPGQGLEWMGG

IYPGNGDTSYNQKFQGRVTMTRDTSTSTVYMELSSLRSEDTAVYYCARGT

VVGDWYFDVWGQGTLVTVSS.
```

In one embodiment, the anti-GPVI antibody or antigen binding fragment thereof for use in the present invention comprises a light chain variable region comprising or consisting of the sequence SEQ ID NO: 8.

```
                                    (SEQ ID NO: 8)
DIQMTQSPSSLSASVGDRVTITCRSSQSLENSNGNTYLNWYQQKPGKAPK

LLIYRVSNRFSGVPSRFSGSGSGTDFTFTISSLQPEDIATYYCLQLTHVP

WTFGQGTKVEITR.
```

In one embodiment, the anti-GPVI antibody or antigen binding fragment thereof for use in the present invention comprises a light chain variable region comprising or consisting of the sequence SEQ ID NO: 9.

```
                                    (SEQ ID NO: 9)
DIQMTQSPSSLSASVGDRVTITCSASQSLENSNGNTYLNWYQQKPGKAPK

LLIYRVSNRFSGVPSRFSGSGSGTDFTLTISSLQPEDFATYYCLQLTHVP

WTFGQGTKVEIKR.
```

In another embodiment of the invention, the anti-GPVI antibody (ACT017 antibody) or antigen binding fragment thereof for use in the present invention comprises a heavy chain variable region comprising or consisting of the sequence SEQ ID NO: 7 and the light chain variable region comprising or consisting of the sequence SEQ ID NO: 8.

In another embodiment of the invention, the anti-GPVI antibody (ACT006 antibody) or antigen binding fragment thereof for use in the present invention comprises the heavy chain variable region comprising or consisting of the sequence SEQ ID NO: 7 and the light chain variable region comprising or consisting of the sequence SEQ ID NO: 9.

According to the invention, one, two, three or more of the amino acids of the heavy chain or light chain variable regions as described hereinabove may be substituted by a different amino acid.

In another embodiment, an antibody (or a fragment thereof) for use in the present invention comprises heavy and light chain variable regions comprising amino acid sequences that are homologous to the amino acid sequences of the ACT017 antibody described herein, and wherein the antibodies retain the desired functional properties of the protein described in the present invention.

In another embodiment, an antibody (or a fragment thereof) for use in the present invention comprises heavy and light chain variable regions comprising amino acid sequences that are homologous to the amino acid sequences of the ACT006 antibody described herein, and wherein the antibodies retain the desired functional properties of the protein described in the present invention.

According to the invention, the heavy chain variable region encompasses sequences that have 60%, 70%, 75%, 80%, 90%, 95%, 96%, 97%, 98%, 99% or more of identity with SEQ ID NO: 7.

According to the invention, the light chain variable region encompasses sequences that have 60%, 70%, 75%, 80%, 90%, 95%, 96%, 97%, 98%, 99% or more of identity with SEQ ID NO: 8 or SEQ ID NO: 9.

In any of the antibodies for use in the present invention (e.g. ACT017 or ACT006), the specified variable region and CDR sequences may comprise conservative sequence modifications. Conservative sequence modifications refer to amino acid modifications that do not significantly affect or alter the binding characteristics of the antibody containing the amino acid sequence. Such conservative modifications include amino acid substitutions, additions and deletions. Modifications can be introduced into an antibody for use in the present invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody for use in the present invention can be replaced with other amino acid residues from the same side chain family and the altered antibody can be tested for retained function (i.e., the properties set forth herein) using the assays described herein.

In one embodiment, the antibody (or fragment thereof) for use in the present invention binds essentially the same epitope as ACT017 or ACT006 antibodies. In the present invention, an antibody that binds essentially the same epitope as ACT017 or ACT006 antibodies will be referred as an ACT017-like or ACT006-like antibody, respectively.

In one embodiment, the antibody (or fragment thereof) for use in the present invention competes for binding to hGPVI with an antibody as described hereinabove, in particular with an antibody selected from ACT017 and ACT006.

In some embodiments of this invention, anti-hGPVI antibodies or fragment thereof comprising VH and VL domains, or CDRs thereof may comprise CH1 domains and/or CL domains, the amino acid sequence of which is fully or substantially human. Where the GPVI binding protein is an antibody intended for human therapeutic use, it is typical for the entire constant region of the antibody, or at least a part thereof, to have a fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Advantageously, the CH1 domain, hinge region, CH2 domain, CH3 domain and CL domain (and CH4 domain if present) may all have a fully or substantially human amino acid sequence. In the context of the constant region of a humanized or chimeric antibody, or an antibody fragment, the term "substantially human" refers to an amino acid sequence identity of at least 70%, or at least 80%, or at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates the use of proteins comprising constant domains of "human" sequence which have been altered, by one or more amino acid additions, deletions or substitutions with respect to the human sequence, excepting those embodiments where the presence of a "fully human" hinge region is expressly required. The presence of a "fully human" hinge region in the anti-hGPVI antibodies for use in the present invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g., by addition or deletion of N- or O-linked glycosylation sites). Depending on the intended use of the antibody, it may be desirable to modify the antibody with respect to its binding properties to Fc receptors, for example to modulate effector function. For example cysteine residue(s) may be introduced in the Fc region, thereby allowing interchain disulfide bond formation in this region. The homodimeric antibody thus generated may have improved effector function. See Caron et al., J. Exp. Med. 176: 1191-1195 (1992) and Shopes, B. J. Immunol. 148: 2918-2922 (1992).

In one embodiment, the heavy chain variable region of sequence SEQ ID NO: 7 is encoded by SEQ ID NO: 10:

```
                                              (SEQ ID NO: 10)
CAGGTTCAGCTGGTTCAGTCAGGGGCTGAGGTGAAGAAGCCTGGAGCCTC

AGTGAAGGTGTCCTGCAAGGCTTCTGGCTACACATTTACCAGTTACAATA

TGCACTGGGTAAGACAGGCTCCTGGACAGGGCCTGGAATGGATGGGAGGT

ATTTATCCAGGAAATGGTGATACTTCCTACAATCAGAAGTTCCAGGGCCG

AGTTACTATGACTCGGGACACTTCCACCTCTACAGTGTACATGGAGCTCA

GCAGCCTGAGATCTGAGGACACCGCGGTCTATTACTGTGCAAGAGGCACC

GTGGTCGGCGACTGGTACTTCGATGTGTGGGGCCAAGGCACCCTGGTCAC

CGTGAGCAGT.
```

In one embodiment, the light chain variable region of sequence SEQ ID NO: 8 is encoded by SEQ ID NO: 11:

```
                                              (SEQ ID NO: 11)
GACATCCAGATGACCCAGAGCCCAAGCAGCCTGAGCGCCAGCGTGGGTGA

CAGAGTGACCATCACCTGTAGAAGTAGTCAGAGCCTTGAGAACAGCAACG

GAAACACCTACCTGAATTGGTACCAGCAGAAGCCAGGTAAGGCTCCAAAG
```

```
CTGCTGATCTACAGAGTTTCCAACCGATTCTCTGGTGTGCCAAGCAGATT

CAGCGGTAGCGGTAGCGGTACCGACTTCACCTTCACCATCAGCAGCCTCC

AGCCAGAGGACATCGCCACCTACTACTGCCTCCAGCTGACTCATGTCCCA

TGGACCTTCGGTCAGGGCACCAAGGTGGAGATCACCCGG.
```

In one embodiment, the light chain variable region of sequence SEQ ID NO: 9 is encoded by SEQ ID NO: 12.

```
                                            (SEQ ID NO: 12)
GACATCCAGATGACCCAGAGCCCAAGCAGCCTGAGCGCCAGCGTGGGTGA

CAGAGTGACCATCACCTGTAGTGCCAGTCAGAGCCTTGAGAACAGCAACG

GAAACACCTACCTGAATTGGTACCAGCAGAAGCCAGGTAAGGCTCCAAAG

CTGCTGATCTACAGAGTTTCCAACCGATTCTCTGGTGTGCCAAGCAGATT

CAGCGGTAGCGGTAGCGGTACCGACTTCACCCTCACCATCAGCAGCCTCC

AGCCAGAGGACTTCGCCACCTACTACTGCCTCCAGCTGACTCATGTCCCA

TGGACCTTCGGTCAGGGCACCAAGGTGGAGATCAAACGC.
```

In one embodiment, the nucleic sequences encoding the anti-GPVI antibody or fragment thereof for use in the present invention are comprised in an expression vector. In one embodiment, the expression vector comprises at least one of SEQ ID NO: 10, SEQ ID NO: 11 and SEQ ID NO: 12 or any sequence having a nucleic acid sequence that shares at least 60%, 70%, 75%, 80%, 90%, 95%, 96%, 97%, 98%, 99% of identity with said SEQ ID NO: 10-12.

In one embodiment, the vector comprises the sequence SEQ ID NO: 10 and a sequence encoding a constant region of a heavy chain. A non-limiting example of a sequence encoding a constant region of a heavy chain is SEQ ID NO: 14.

```
                                            (SEQ ID NO: 14)
GCCTCCACCAAGGGTCCCTCAGTCTTCCCACTGGCACCCTCCTCCAAGAG

CACCTCTGGTGGCACAGCTGCCCTGGGCTGCCTGGTCAAGGACTACTTCC

CAGAACCAGTGACTGTGTCATGGAACTCAGGCGCCCTGACCAGCGGCGTG

CACACCTTCCCTGCTGTCTTGCAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTCGAGCCT

AAGTCATGCGACAAGACTCAC.
```

In one embodiment, the vector comprises the sequence SEQ ID NO: 11 or SEQ ID NO: 12 and a sequence encoding a constant region of a light chain. A non-limiting example of a sequence encoding a constant region of a light chain is SEQ ID NO: 15.

```
                                            (SEQ ID NO: 15)
ACTGTGGCTGCACCAAGTGTGTTCATCTTCCCACCTAGCGATGAGCAGTT

GAAATCTGGAACTGCCTCTGTCGTGTGCCTCCTGAACAACTTCTACCCAC

GGGAGGCCAAGGTACAGTGGAAGGTGGATAACGCCCTCCAATCCGGTAAC

TCCCAGGAGAGTGTCACAGAGCAAGATAGCAAGGACAGCACCTACAGCCT

CAGCAGCACCCTGACTCTGAGCAAAGCAGACTACGAGAAGCACAAGGTCT

ACGCCTGCGAAGTCACCCATCAGGGCCTGAGTTCCCCTGTCACAAAGAGC

TTCAACCGGGGAGAGTGT.
```

In one embodiment, the vector comprises a sequence encoding a signal peptide. Non-limiting examples of signal peptides sequences include, but are not limited to, SEQ ID NO: 16 and SEQ ID NO: 17.

```
                                            (SEQ ID NO: 16)
ATGGATATGCGTGTACCAGCTCAACTACTTGGACTTCTATTGCTTTGGCT

TCGTGGTGCTAGATGT.

(SEQ ID NO: 17)
ATGGACTGGACTTGGAGAATCCTATTCTTGGTTGCTGCAGCTACAGGTGC

TCATTCA.
```

In one embodiment, the vector comprises SEQ ID NO: 10, and a sequence encoding a constant region of a heavy chain (such as, for example, SEQ ID NO: 14), and a signal peptide sequence. An example of such a vector is a vector comprising SEQ ID NO: 18. SEQ ID NO: 18 further comprises cloning sites.

```
                                            (SEQ ID NO: 18)
GCGGCCGCCACCATGGACTGGACTTGGAGAATCCTATTCTTGGTTGCTGC

AGCTACAGGTGCTCATTCACAGGTTCAGCTGGTTCAGTCAGGGGCTGAGG

TGAAGAAGCCTGGAGCCTCAGTGAAGGTGTCCTGCAAGGCTTCTGGCTAC

ACATTTACCAGTTACAATATGCACTGGGTAAGACAGGCTCCTGGACAGGG

CCTGGAATGGATGGGAGGTATTTATCCAGGAAATGGTGATACTTCCTACA

ATCAGAAGTTCCAGGGCCGAGTTACTATGACTCGGGACACTTCCACCTCT

ACAGTGTACATGGAGCTCAGCAGCCTGAGATCTGAGGACACCGCGGTCTA

TTACTGTGCAAGAGGCACCGTGGTCGGCGACTGGTACTTCGATGTGTGGG

GCCAAGGCACCCTGGTCACCGTGAGCAGTGCCTCCACCAAGGGTCCCTCA

GTCTTCCCACTGGCACCCTCCTCCAAGAGCACCTCTGGTGGCACAGCTGC

CCTGGGCTGCCTGGTCAAGGACTACTTCCCAGAACCAGTGACTGTGTCAT

GGAACTCAGGCGCCCTGACCAGCGGCGTGCACACCTTCCCTGCTGTCTTG

CAGTCCTCAGGACTCTACTCCCTCAGCAGCGTGGTGACCGTGCCCTCCAG

CAGCTTGGGCACCCAGACCTACATCTGCAACGTGAATCACAAGCCCAGCA

ACACCAAGGTGGACAAGAAAGTCGAGCCTAAGTCATGCGACAAGACTCAC

TGATGAGGATCC.
```

In one embodiment, the vector comprises SEQ ID NO: 8, and a sequence encoding a constant region of a light chain (such as, for example, SEQ ID NO: 15), and a signal peptide sequence. An example of such a vector is a vector comprising SEQ ID NO: 19. SEQ ID NO: 19 further comprises cloning sites.

```
                                            (SEQ ID NO: 19)
GACGTCACCATGGATATGCGTGTACCAGCTCAACTACTTGGACTTCTATT

GCTTTGGCTTCGTGGTGCTAGATGTGACATCCAGATGACCCAGAGCCCAA

GCAGCCTGAGCGCCAGCGTGGGTGACAGAGTGACCATCACCTGTAGAAGT
```

```
-continued
AGTCAGAGCCTTGAGAACAGCAACGGAAACACCTACCTGAATTGGTACCA

GCAGAAGCCAGGTAAGGCTCCAAAGCTGCTGATCTACAGAGTTTCCAACC

GATTCTCTGGTGTGCCAAGCAGATTCAGCGGTAGCGGTAGCGGTACCGAC

TTCACCTTCACCATCAGCAGCCTCCAGCCAGAGGACATCGCCACCTACTA

CTGCCTCCAGCTGACTCATGTCCCATGGACCTTCGGTCAGGGCACCAAGG

TGGAGATCACCCGGACTGTGGCTGCACCAAGTGTGTTCATCTTCCCACCT

AGCGATGAGCAGTTGAAATCTGGAACTGCCTCTGTCGTGTGCCTCCTGAA

CAACTTCTACCCACGGGAGGCCAAGGTACAGTGGAAGGTGGATAACGCCC

TCCAATCCGGTAACTCCCAGGAGAGTGTCACAGAGCAAGATAGCAAGGAC

AGCACCTACAGCCTCAGCAGCACCCTGACTCTGAGCAAAGCAGACTACGA

GAAGCACAAGGTCTACGCCTGCGAAGTCACCCATCAGGGCCTGAGTTCCC

CTGTCACAAAGAGCTTCAACCGGGGAGAGTGTTGATGATATC.
```

In one embodiment, the vector comprises SEQ ID NO: 9, and a sequence encoding a constant region of a light chain (such as, for example, SEQ ID NO: 15), and a signal peptide sequence. An example of such a vector is a vector comprising SEQ ID NO: 20.

SEQ ID NO: 20 further comprises cloning sites.

```
                                            (SEQ ID NO: 20)
GACGTCACCATGGATATGCGTGTACCAGCTCAACTACTTGGACTTCTATT

GCTTTGGCTTCGTGGTGCTAGATGTGACATCCAGATGACCCAGAGCCCAA

GCAGCCTGAGCGCCAGCGTGGGTGACAGAGTGACCATCACCTGTAGTGCC

AGTCAGAGCCTTGAGAACAGCAACGGAAACACCTACCTGAATTGGTACCA

GCAGAAGCCAGGTAAGGCTCCAAAGCTGCTGATCTACAGAGTTTCCAACC

GATTCTCTGGTGTGCCAAGCAGATTCAGCGGTAGCGGTAGCGGTACCGAC

TTCACCCTCACCATCAGCAGCCTCCAGCCAGAGGACTTCGCCACCTACTA

CTGCCTCCAGCTGACTCATGTCCCATGGACCTTCGGTCAGGGCACCAAGG

TGGAGATCAAACGCACTGTGGCTGCACCAAGTGTGTTCATCTTCCCACCT

AGCGATGAGCAGTTGAAATCTGGAACTGCCTCTGTCGTGTGCCTCCTGAA

CAACTTCTACCCACGGGAGGCCAAGGTACAGTGGAAGGTGGATAACGCCC

TCCAATCCGGTAACTCCCAGGAGAGTGTCACAGAGCAAGATAGCAAGGAC

AGCACCTACAGCCTCAGCAGCACCCTGACTCTGAGCAAAGCAGACTACGA

GAAGCACAAGGTCTACGCCTGCGAAGTCACCCATCAGGGCCTGAGTTCCC

CTGTCACAAAGAGCTTCAACCGGGGAGAGTGTTGATGATATC.
```

In one embodiment, the vector as described hereinabove is comprised in an isolated host cell. Said host cell may be used for the recombinant production of the antibodies for use in the present invention. In an embodiment, host cells may be prokaryote, yeast, or eukaryote cells preferably mammalian cells, such as, for example: monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); mouse myeloma cells SP2/0-AG14 (ATCC CRL 1581; ATCC CRL 8287) or NSO (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art. It should be noted that the term "host cell" generally refers to a cultured cell line. Whole human beings into which an expression vector encoding an antigen binding protein for use according to the invention has been introduced are explicitly excluded from the definition of a "host cell".

Methods for producing an anti-hGPVI antibody or antigen binding fragment thereof for use in the present invention are well known in the art. Examples of suitable methods comprise culturing host cells containing the isolated polynucleotide sequence encoding the anti-hGPVI antibody or fragment thereof for use in the present invention under conditions suitable for expression of the anti-hGPVI antibody or fragment thereof, and recovering the expressed anti-hGPVI antibody or fragment thereof. This recombinant process can be used for large scale production of anti-hGPVI antibodies or fragment thereof for use in the present invention, including monoclonal antibodies intended for in vivo therapeutic uses. These processes are available in the art and will be known by the skilled person.

In one embodiment, the protein for use in the present invention may be purified by chromatography, preferably by affinity chromatography, more preferably by affinity chromatography on protein L agarose.

Therefore, in one embodiment, the protein for use in the present invention comprises a domain for binding protein L (PpL). Methods for transferring PpL-binding activity onto proteins of the invention are described in Muzard et al., Analytical Biochemistry 388, 331-338, 2009 and in Lakhrif et al., MAbs. 2016; 8(2):379-88, which are incorporated herein by reference.

Fragments and derivatives of antibodies for use in the present invention (which are encompassed by the term "antibody" or "antibodies" as used in this application, unless otherwise stated or clearly contradicted by context), preferably a ACT017-like or ACT006-like antibody, can be produced by techniques that are known in the art. "Fragments" comprise a portion of the intact antibody, generally the antigen binding site or variable region. Examples of antibody fragments include Fab, Fab', Fab'-SH, F (ab')$_2$, and Fv fragments; diabodies; any antibody fragment that is a protein having a primary structure consisting of one uninterrupted sequence of contiguous amino acid residues (referred to herein as a "single-chain antibody fragment" or "single chain protein"), including without limitation (1) single-chain Fv molecules (2) single chain proteins containing only one light chain variable domain, or a fragment thereof that contains the three CDRs of the light chain variable domain, without an associated heavy chain moiety and (3) single chain proteins containing only one heavy chain variable region, or a fragment thereof containing the three CDRs of the heavy chain variable region, without an associated light chain moiety; and multispecific antibodies formed from antibody fragments. Fragments of the present antibodies can be obtained using standard methods. For instance, Fab or F(ab')₂ fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al., Cytokines 16 (3): 106-119 (2001) and Delgado et al., Br. J. Cancer 73 (2): 175-182 (1996), the disclosures of which are incorporated herein by reference.

Alternatively, the DNA encoding an antibody for use in the present invention, preferably an ACT017-like or ACT006-like antibody, may be modified so as to encode a fragment. The modified DNA is then inserted into an expression vector and used to transform or transfect an appropriate cell, which then expresses the desired fragment.

Another object of the invention is a composition for treating or for use in treating a GPVI-related condition in a subject in need thereof, wherein said composition comprises at least one isolated humanized protein binding to human Glycoprotein VI (hGPVI) as described here above, and wherein said composition is administered (or is to be administered) during at least 2 hours to the subject, preferably during at least 4 to 6 hours.

Another object of the invention is a pharmaceutical composition for treating or for use in treating a GPVI-related condition in a subject in need thereof, wherein said pharmaceutical composition comprises at least one isolated humanized protein binding to human Glycoprotein VI (hGPVI) as described here above and at least one pharmaceutically acceptable excipient, and wherein said pharmaceutical composition is administered (or is to be administered) during at least 2 hours to the subject, preferably during at least 4 to 6 hours.

Pharmaceutically acceptable excipients that may be used in these compositions include, but are not limited to, ion exchangers, alumina, aluminum stearate, lecithin, serum proteins, such as human serum albumin, buffer substances such as acetates, citrates, phosphates, glycine, sorbic acid, potassium sorbate, sugars such as glucose, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the invention is a pharmaceutical composition for treating or for use in treating a GPVI-related condition in a subject in need thereof, wherein the pH of the pharmaceutical composition is comprised between 4 to 6 and preferably is of about 5.0.

Another object of the invention is a medicament for treating or for use in treating a GPVI-related condition in a subject in need thereof, wherein said medicament comprises at least one isolated humanized protein binding to human Glycoprotein VI (hGPVI) as described here above, and wherein said medicament is administered (or is to be administered) during at least 2 hours to the subject, preferably during at least 4 to 6 hours.

In one embodiment, the composition, pharmaceutical composition or medicament for use in the present invention further comprises another agent useful for treating a GPVI-related condition, such as, for example a thrombolytic agent. One example of thrombolytic agent is t-PA, including native t-PA and recombinant t-PA, as well as modified forms of t-PA that retain the enzymatic and/or fibrinolytic activity of native t-PA. As used herein, t-PA has its general meaning in the art and refers to tissue-type plasminogen activator. The enzymatic activity of a modified form of t-PA may be measured by assessing the ability of the molecule to convert plasminogen to plasmin. The fibrinolytic activity of a modified form of t-PA may be determined by any in vitro clot lysis test known in the art. T-PA is commercially available as alteplase (Activase® or Actilyse®). Recombinant t-PA has been described in the art and is known by the skilled artisan. Modified forms of t-PA has been described in the art and is known by the skilled artisan, and include, without limitation, t-PA having deleted or substituted amino acids or domains, modified glycosylation status, and variants conjugated to or fused with other molecules. Examples of modified forms of t-PA were described, for example, in EP0352119, WO93/24635, EP0382174 and WO2013/034710, which are incorporated herein by reference.

In one embodiment, the composition, pharmaceutical composition or medicament for use in the present invention further comprises a mutated t-PA as described in WO2013/034710.

In one embodiment, said mutated t-PA comprises the sequence SEQ ID NO: 25 (corresponding to human wt t-PA mature form) or SEQ ID NO: 26 (corresponding to human wt t-PA first chain of tc-t-PA), preferably consisting of SEQ ID NO: 25 or of the association of SEQ ID NO:26 and SEQ ID NO:27 (corresponding to human wt t-PA second chain of tc-t-PA), or variant thereof having at least 80% identity, wherein said sequence comprises a mutation consisting of the replacement of any amino acid of the Lysine Binding Site of SEQ ID NO: 25 or SEQ ID NO:26 by a hydrophilic amino acid chosen from arginine, aspartic acid, glutamic acid, lysine, asparagine, glutamine, serine, threonine, tyrosine and histidine, preferably by arginine, and/or a mutation consisting of the replacement of arginine in position 275 of SEQ ID NO: 25 or SEQ ID NO:26 by serine.

In one embodiment, said mutated t-PA comprises the sequence SEQ ID NO: 25 (corresponding to human wt t-PA mature form) or SEQ ID NO: 26 (corresponding to human wt t-PA first chain of two chain t-PA), preferably consisting of SEQ ID NO: 25 or of the association of SEQ ID NO:26 and SEQ ID NO:27 (corresponding to human wt t-PA second chain of two chain t-PA), or variant thereof having at least 80% identity, wherein said sequence comprises a mutation consisting of the replacement of tryptophan in position 253 of SEQ ID NO: 25 or SEQ ID NO:26 by a hydrophilic amino acid chosen from arginine, aspartic acid, glutamic acid, lysine, asparagine, glutamine, serine, threonine, tyrosine and histidine, preferably by arginine, and/or a mutation consisting of the replacement of arginine in position 275 of SEQ ID NO: 25 or SEQ ID NO:26 by serine.

In one embodiment, said mutated t-PA further comprises at least one of the following mutations:
  the replacement of proline in position 125 of SEQ ID NO:25 or SEQ ID NO:26 by arginine,
  the deletion of the Finger domain in the N-terminus and/or the deletion of the EGF-like domain, in SEQ ID NO:25 or SEQ ID NO:26, and/or the replacement of asparagine in position 117 of SEQ ID NO:25 or SEQ ID NO:26 by glutamine,
  the replacement of threonine in position 103 of SEQ ID NO:25 or SEQ ID NO:26 by asparagine, and/or the replacement of asparagine in position 117 of SEQ ID NO:25 or SEQ ID NO:26 by glutamine, and/or the replacement of lysine-histidine-arginine-arginine (KHRR) in positions 296 to 299 of SEQ ID NO:25 by alanine-alanine-alanine-alanine (AAAA), the replacement of cysteine in position 84 of SEQ ID NO:25 or SEQ ID NO:26 by serine, the replacement of arginine in position 275 of SEQ ID NO:25 or SEQ ID NO:26 by glutamic acid or glycine, and/or the deletion of the Kringle 1 domain in SEQ ID NO:25 or SEQ ID NO:26.

Therefore, in one embodiment, the composition, pharmaceutical composition or medicament for use in the present invention comprises at least one isolated humanized protein binding to human Glycoprotein VI (hGPVI) as described here above, preferably at least one anti-hGPVI antibody as described hereinabove or antigen binding fragment thereof, and t-PA (either in a native, recombinant or modified form).

One object of the invention is a kit of part comprising, in a first part, at least one isolated humanized protein binding to human Glycoprotein VI (hGPVI) as described hereinabove (preferably at least one isolated anti-hGPVI antibody or antigen binding fragment thereof as described hereinabove) and, in a second part, at least one t-PA (either in a native, recombinant or modified form).

Another object is thus a kit of part as described hereinabove, for use in the treatment of a GPVI-related condition in a subject in need thereof.

In an embodiment, the protein for use in the present invention is an anti-hGPVI antibody or antigen binding fragment thereof that inhibits GPVI signaling and/or signaling of a ligand of GPVI. As used herein, the term "inhibit" means that the protein for use in the present invention is capable of blocking, reducing, preventing or neutralizing GPVI interaction with its ligands, GPVI signaling and/or the activation of molecules from the GPVI signaling pathway.

Examples of ligands of GPVI include, but are not limited to, collagen, fibrin, fibronectin, vitronectin and laminins.

In an embodiment, the protein for use in the present invention is a neutralizing anti-hGPVI antibody or fragment thereof.

In an embodiment, the protein for use in the present invention inhibits the binding of GPVI to a ligand thereof (such as, for example, collagen, fibrin or any other GPVI ligand capable of inducing downstream signaling and platelet activation).

In an embodiment, the protein for use in the present invention inhibits and/or prevents platelet activation, secretion and aggregation in response to a ligand of GPVI, such as, for example, collagen. In an embodiment, the protein for use in the present invention inhibits and/or prevents platelet adhesion to a ligand of GPVI, such as, for example, collagen.

In an embodiment, the protein for use in the present invention inhibits and/or prevents GPVI-dependent thrombin production in response to a ligand of GPVI, such as, for example, fibrin. In an embodiment, the protein for use in the present invention inhibits and/or prevent platelet-catalyzed thrombin production in response to collagen and/or to tissue factor.

In an embodiment, the protein for use in the present invention inhibits and/or prevents platelet recruitment by a ligand of GPVI (such as, for example, fibrin) via GPVI.

In one embodiment, the protein for use in the present invention induces saturation of platelets in whole blood or in platelet rich plasma when present at a concentration ranging from about 1 to about 200 µg/mL, preferably from about 2 to about 100 µg/mL, and more preferably from about 5 to about 50 µg/mL.

In one embodiment, the protein for use in the present invention inhibits collagen-induced platelet aggregation when used at a concentration of at least about 15 µg/mL, preferably of at least about 10 µg/mL. Preferably, the protein for use in the present invention fully inhibits collagen-induced platelet aggregation when used at such concentrations.

In one embodiment, the IC50 of the protein for use in the present invention for inhibiting collagen-induced platelet aggregation ranges from about 0.5 to about 10 µg/mL, preferably from about 1 to about 6 µg/mL, more preferably from about 2 to about 3.2 µg/mL.

In one embodiment, the concentration of the protein for use in the present invention reducing by 50% the velocity of collagen-induced platelet aggregation ranges from about 0.5 to about 5 µg/mL, preferably from about 1 to about 3 µg/mL, more preferably of about 2 µg/mL.

In one embodiment, the concentration of the protein for use in the present invention reducing the intensity of collagen-induced platelet aggregation ranges from about 0.5 to about 10 µg/mL, preferably from about 1 to about 6 µg/mL, more preferably of about 3.2 µg/mL.

In one embodiment, the protein for use in the present invention does not induce depletion of GPVI when administered in vivo, such as, for example, when administered at a dose ranging from 0.01 to 500 mg.

In one embodiment, the protein for use in the present invention does not induce a decrease in platelet count, i.e., thrombocytopenia, when administered in vivo, such as, for example, when administered at a dose ranging from 0.01 to 500 mg.

Examples of GPVI-related conditions are well known in the art and include, without limitation, inflammation, thrombosis, disorders associated with abnormal or aberrant megakaryocyte and/or platelet proliferation, differentiation, morphology, migration, aggregation, degranulation and/or function, thrombotic disorders (such as, for example, thrombotic occlusion of coronary arteries), diseases exhibiting quantitative or qualitative platelet dysfunction and diseases displaying endothelial dysfunction, cerebral vascular diseases, coronary diseases, disorders resulting from any blood vessel insult that can result in platelet aggregation, disorders associated with aberrant signal transduction in response to ligands of GPVI, disorders associated with aberrant levels of GPVI expression and/or activity either in cells that normally express GPVI or in cells that do not express GPVI, bone marrow and peripheral blood or disorders in which platelets contribute by modulating inflammatory responses.

In one embodiment, said GPVI-related condition is a cardiovascular disease selected from arterial and venous thrombosis, restenosis, acute coronary syndrome, cerebrovascular accidents due to atherosclerosis, myocardial infarction, pulmonary embolism, critical limb ischemia and peripheral artery disease.

In one embodiment, said GPVI-related condition is a venous thrombosis. In one embodiment, said GPVI-related condition is a restenosis. In one embodiment, said GPVI-related condition is an acute coronary syndrome. In one embodiment, said GPVI-related condition is cerebrovascular accidents due to atherosclerosis. In one embodiment, said GPVI-related condition is a myocardial infarction. In one embodiment, said GPVI-related condition is a pulmonary embolism. In one embodiment, said GPVI-related condition is a critical limb ischemia. In one embodiment, said GPVI-related condition is a peripheral artery disease.

In one embodiment, the protein, composition, pharmaceutical composition or medicament as described hereinabove is used to modulate leukocyte-platelet in inflammation and/or thrombosis. Therefore, according to an embodiment, the protein, composition, pharmaceutical composition or medicament as described hereinabove is used to treat inflammation and/or thrombosis.

In one embodiment, the protein, composition, pharmaceutical composition or medicament as described hereinabove is used to modulate, preferably to prevent, platelet adhesion aggregation and degranulation.

In one embodiment, the protein, composition, pharmaceutical composition or medicament as described hereinabove is used to treat thrombotic disorders (such as, for example, thrombotic occlusion of coronary arteries), diseases exhibiting quantitative or qualitative platelet dysfunction and diseases displaying endothelial dysfunction. These diseases include, but are not limited to, coronary artery and cerebral artery diseases.

In one embodiment, the protein, composition, pharmaceutical composition or medicament as described hereinabove is used to treat cerebral vascular diseases, including ischemic stroke, venous thromboembolism diseases (such as, for example, diseases involving leg swelling, pain and ulceration, pulmonary embolism, abdominal venous thrombosis), thrombotic microangiopathies, vascular purpura.

In one embodiment, the protein, composition, pharmaceutical composition or medicament as described hereinabove is used to treat coronary diseases (such as, for example, cardiovascular diseases including unstable angina pectoris, myocardial infarction, acute myocardial infarction, coronary artery disease, coronary revascularization, coronary restenosis, ventricular thromboembolism, atherosclerosis, coronary artery disease (e. g., arterial occlusive disorders), plaque formation, cardiac ischemia, including complications related to coronary procedures, such as percutaneous coronary artery angioplasty (balloon angioplasty) procedures). With respect to coronary procedures, such treatment can be achieved via administration of a protein as described above prior to, during, or subsequent to the procedure. In a preferred embodiment, such administration can be utilized to prevent acute cardiac ischemia following angioplasty.

In one embodiment, the protein, composition, pharmaceutical composition or medicament as described hereinabove is used to treat disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e. g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Further, in certain embodiments, it is preferred that the protein does not affect other platelet attributes or functions, such as agonist-induced platelet shape change (e.g., GPIb-vWF-mediated platelet activation), release of internal platelet granule components, activation of signal transduction pathways or induction of calcium mobilization upon platelet activation by agonists that do not interact with GPVI.

In one embodiment, the protein, composition, pharmaceutical composition or medicament as described hereinabove is used to treat disorders associated with aberrant signal transduction in response to ligands of GPVI (including, without limitation, collagen, fibrin, fibronectin, vitronectin and laminins) or to other extracellular matrix proteins.

In one embodiment, the protein, composition, pharmaceutical composition or medicament as described hereinabove is used to treat disorders associated with aberrant levels of GPVI expression and/or activity either in cells that normally express GPVI or in cells that do not express GPVI. For example, the protein can be used to modulate disorders associated with aberrant expression of GPVI in cancerous (e. g., tumor) cells that do not normally express GPVI. Such disorders can include, for example, ones associated with tumor cell migration and progression to metastasis.

In one embodiment, the protein, composition, pharmaceutical composition or medicament as described hereinabove is used to modulate immunoregulatory functions of platelets.

In one embodiment, the protein, composition, pharmaceutical composition or medicament as described hereinabove is used to treat disorders bone marrow and peripheral blood.

In one embodiment, the protein, composition, pharmaceutical composition or medicament as described hereinabove is used to treat disorders in which platelets contribute by modulating inflammatory responses including, without limitation, sustained or prolonged inflammation associated with infection, arthritis, fibrosis or disorders in which platelets modulate cell functions including, without limitation, cancer cells proliferation and/or dissemination.

Further examples of diseases, disorders or conditions related to GPVI include, but are not limited to, cardiovascular diseases and/or cardiovascular events, such as, for example, arterial thrombosis including atherothrombosis, ischemic events, acute coronary artery syndrome, myocardial infarction (heart attack), acute cerebrovascular ischemia (stroke), percutaneous coronary intervention, stenting thrombosis, ischemic, restenosis, ischemia, (acute and chronic), diseases of the aorta and its branches (such as aortic aneurysm, thrombosis), peripheral artery disease, venous thrombosis, acute phlebitis and pulmonary embolism, cancer-associated thrombosis (Trousseau syndrome), inflammatory thrombosis and thrombosis associated to infection.

In one embodiment, the pharmaceutical composition or medicament of the invention is for treating or for use in treating arterial or venous thrombosis, restenosis, acute coronary syndrome or cerebrovascular accidents due to atherosclerosis, preferably thrombosis.

In one embodiment, the subject is affected by, preferably is diagnosed with a disease, disorder or condition related to GPVI, preferably a cardiovascular disease and/or event.

In one embodiment, the subject experienced a cardiovascular event (such as, for example, thrombosis, stroke, myocardial infarction or a cerebrovascular accident) less than 48 hours, preferably less than 24 hours, 12 hours or less, before the administration of the protein for use in the present invention.

In one embodiment, the subject receive a protein, composition, pharmaceutical composition or medicament as described hereinabove as part of a treatment protocol.

In one embodiment, said treatment protocol further comprises, before, concomitantly or after the administration of the protein of the invention, the administration of another agent useful for treating a GPVI-related condition, such as, for example a thrombolytic agent, preferably t-PA (including native t-PA and recombinant t-PA, as well as modified forms of t-PA that retain the enzymatic and/or fibrinolytic activity of native t-PA).

In one embodiment, said treatment protocol further comprises, before, concomitantly or after the administration of the protein of the invention, the treatment of the subject by endovascular treatment and/or by thrombectomy (also known as embolectomy).

Therefore, in one embodiment, the subject to be treated was previously treated or is to be treated by endovascular treatment and/or by thrombectomy.

In one embodiment, a dose of the protein for use in the present invention ranging from about 0.5 mg/kg to about 50 mg/kg is administered (or is to be administered) to the patient, preferably ranging from about 1 mg/kg to about 32 mg/kg, more preferably of about 8 mg/kg. In another embodiment, a dose of humanized protein ranging from about 2.5 mg/kg to about 25 mg/kg, preferably from about 5 mg/kg to about 15 mg/kg, more preferably of about 8 mg/kg is to be administered to the patient. In one embodiment, a dose of the protein for use in the present invention of about 0.5 mg/kg, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or of about 50 mg/kg is administered (or is to be administered) to the subject.

In one embodiment, a dose of the protein for use in the present invention ranging from about 30 mg to about 3000 mg is administered (or is to be administered) to the patient, preferably ranging from about 60 mg to about 2000 mg, more preferably of about 100 to about 1000 mg, and even more preferably of about 500 mg. In one embodiment, a dose of the protein for use in the present invention of about 30, 60, 62.5, 90, 100, 125, 150, 175, 200, 225, 250, 275, 300, 325, 350, 375, 400, 450, 500, 550, 600, 650, 700, 750, 800, 850, 900, 950, 1000, 1500, 2000, 2500 or of about 3000 mg is administered (or is to be administered) to the subject. In another embodiment, a dose of the protein for use in the present invention ranges from about 100 mg to about 2000 mg, from about 125 mg to about 2000 mg, preferably from about 250 mg to about 1000 mg or from about 500 mg to about 1000 mg.

The composition will be formulated for administration to the subject. The compositions may be administered parenterally, by inhalation spray, rectally, nasally, or via an implanted reservoir. The term administration used herein includes subcutaneous, intravenous, intramuscular, intra-articular, intra-synovial, intrasternal, intrathecal, intrahepatic, intralesional and intracranial injection or infusion techniques.

In one embodiment, the protein for use in the present invention is injected, preferably by intravenous infusion. In another embodiment, the protein for use in the present invention is injected intraperitoneally. In another embodiment, the protein for use in the present invention is injected intradermally.

Examples of forms adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

Sterile injectable forms of the compositions may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, the protein for use in the present invention is administered (or is to be administered) to the subject during about 2 hours, 2.5, 3, 3.5, 4, 4.5, 5, 5.5, 6, 6.5, 7, 7.5, 8, 8.5, 9, 9.5, 10, 10.5, 11, 11.5 or during about 12 hours.

In one embodiment, the protein for use in the present invention is continuously administered to the subject during at least 2 hours, preferably during at least 4 to 6 hours (e.g. during about 2 hours, 2.5, 3, 3.5, 4, 4.5, 5, 5.5, 6, 6.5, 7, 7.5, 8, 8.5, 9, 9.5, 10, 10.5, 11, 11.5 or during about 12 hours). As used herein, the terms "continuously administered" refers to the administration of a compound for a prolonged period of time with a substantially constant speed of administration.

In another embodiment, a first bolus of the protein is injected, followed by the continuous administration of the remaining dose of the protein.

In one embodiment, said first bolus administration comprises about 10 to 50%, preferably about 20% of the total dosage of the isolated humanized protein to be administered. In one embodiment, said first bolus administration comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50% of the total dosage of the isolated humanized protein to be administered.

In one embodiment, said first bolus is administered in about 5 to 30 minutes, preferably in about 15 minutes.

In one embodiment, about 20% of the total dosage of the protein for use in the present administration are administered during the first 15 minutes of the administration, followed by a continuous administration of the remaining 80% during the next 5 hours 45 minutes.

In one embodiment, said specific administration regimen (continued administration during at least 2 hours, with optionally a first bolus) allows a prolonged effect of the protein, which may be observed after the end of administration of said protein, as demonstrated in the Examples. In one embodiment, the effect of the protein on platelet aggregation is observed for at least about 1, 2, 3, 4, 5, 6, 12, 18, 24, 36 or 48 hours after the end of the administration of the protein.

In one embodiment, a protein for use in the present invention present in a pharmaceutical composition can be supplied at a concentration ranging from about 1 to about 100 mg/mL, such as, for example, at a concentration of 1 mg/mL, 5 mg/mL, 10 mg/mL, 50 mg/mL or 100 mg/mL. In one embodiment, the protein is supplied at a concentration of about 10 mg/mL in either 100 mg (10 mL) or 500 mg (50 mL) single-use vials.

In one embodiment, the pharmaceutical composition may comprise a protein of the invention in PBS pH 7.2-7.7.

In one embodiment, the pharmaceutical composition may comprise a protein of the invention in sodium citrate buffer 20 mM, NaCl 130 mM, pH 5.0.

Another object of the invention is a method of treating a GPVI-related condition, wherein said method comprises administering to a subject in need thereof an isolated humanized protein binding to hGPVI as described hereinabove, or a composition, pharmaceutical composition or medicament as described hereinabove. According to the invention, the method of the invention comprises administering said protein, composition, pharmaceutical composition or medicament during at least 2 hours to the subject, preferably during at least 4 to 6 hours.

In one embodiment, the method of treating a GPVI-related condition of the present invention further comprises treating the patient with endovascular treatment and/or thrombectomy. In one embodiment, said endovascular treatment and/or thrombectomy is carried out before, concomitantly or after the administration of the protein (preferably the antibody) of the present invention.

In one embodiment, the method of treating a GPVI-related condition of the present invention further comprises a step of administering another agent useful for treating a GPVI-related condition, such as, for example a thrombolytic agent, preferably t-PA (including native t-PA and recombinant t-PA, as well as modified forms of t-PA that retain the enzymatic and/or fibrinolytic activity of native t-PA). In one embodiment, said additional agent is administered before, concomitantly or after the administration of the protein (preferably the antibody) of the present invention.

In one embodiment, the method of the invention comprises administering a dose of the protein as described in the present invention ranging from about 0.5 mg/kg to about 50 mg/kg, preferably ranging from about 1 mg/kg to about 32 mg/kg, more preferably of about 8 mg/kg. In another embodiment, the method of the invention comprises administering a dose of the protein as described in the present invention ranging from about 2.5 mg/kg to about 25 mg/kg, preferably from about 5 mg/kg to about 15 mg/kg, more preferably of about 8 mg/kg. In one embodiment, the method of the invention comprises administering a dose of the protein as described in the present invention of about 0.5 mg/kg, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or of about 50 mg/kg.

In one embodiment, the method of the invention comprises administering a dose of the protein as described in the present invention ranging from about 30 mg to about 3000 mg, preferably ranging from about 60 mg to about 2000 mg, more preferably of about 100 to about 1000 mg, and even more preferably of about 500 mg. In one embodiment, the method of the invention comprises administering a dose of the protein as described in the present invention of about 30, 60, 62.5, 90, 100, 125, 150, 175, 200, 225, 250, 275, 300, 325, 350, 375, 400, 450, 500, 550, 600, 650, 700, 750, 800, 850, 900, 950, 1000, 1500, 2000, 2500 or of about 3000 mg. In another embodiment, the method of the invention comprises administering a dose of the protein as described in the present invention ranging from about 100 mg to about 2000 mg, from about 125 mg to about 2000 mg, preferably from about 250 mg to about 1000 mg or from about 500 mg to about 1000 mg.

In one embodiment, the protein as described in the present invention is injected, preferably by intravenous infusion.

In one embodiment, the method of the invention comprises administering the protein during about 2 hours, 2.5, 3, 3.5, 4, 4.5, 5, 5.5, 6, 6.5, 7, 7.5, 8, 8.5, 9, 9.5, 10, 10.5, 11, 11.5 or during about 12 hours.

In one embodiment, the method of the invention comprises continuously administering the protein during at least 2 hours, preferably during at least 4 to 6 hours (e.g., during about 2 hours, 2.5, 3, 3.5, 4, 4.5, 5, 5.5, 6, 6.5, 7, 7.5, 8, 8.5, 9, 9.5, 10, 10.5, 11, 11.5 or during about 12 hours).

In another embodiment, the method of the invention comprises administering a first bolus of the protein, followed by the continuous administration of the remaining dose of the protein.

In one embodiment, said first bolus administration comprises about 10 to 50%, preferably about 20% of the total dosage of the isolated humanized protein to be administered. In one embodiment, said first bolus administration comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50% of the total dosage of the isolated humanized protein to be administered.

In one embodiment, said first bolus is administered in about 5 to 30 minutes, preferably in about 15 minutes.

In one embodiment, about 20% of the total dosage of the protein for use in the present administration are administered during the first 15 minutes of the administration, followed by a continuous administration of the remaining 80% during the next 5 hours 45 minutes.

In one embodiment, the method of the invention is for inhibiting GPVI receptor function and downstream signalling, thereby treating a GPVI related condition.

In one embodiment, the method for inhibiting GPVI receptor function and downstream signalling does not impact platelet count, expression of GPVI at the platelet surface nor bleeding time.

In one embodiment, the method for inhibiting GPVI receptor function and downstream signalling is efficient and reversible.

In one embodiment, the method of the invention is for inhibiting the binding of GPVI to its ligands (preferably, but not exclusively, collagen), thereby treating a GPVI related condition.

In one embodiment, the method for inhibiting the binding of GPVI to its ligands does not impact platelet count, expression of GPVI at the platelet surface nor bleeding time.

In one embodiment, the method for inhibiting the binding of GPVI to its ligands is efficient and reversible.

In one embodiment, the method of the invention is for inhibiting and/or preventing platelet adhesion to collagen, thereby treating a GPVI related condition.

In one embodiment, the method of the invention is for inhibiting and/or preventing collagen-induced platelet aggregation, thereby treating a GPVI related condition In one embodiment, the method of the invention is for inhibiting and/or preventing platelet activation, in particular platelet aggregation, in response to collagen, thereby treating a GPVI related condition.

In one embodiment, the method of the invention is for inhibiting and/or preventing thrombin production in response to collagen and/or to tissue factor, thereby treating a GPVI related condition.

In one embodiment, the method of the invention is for inhibiting the binding of GPVI to fibrin, thereby treating a GPVI related condition.

In one embodiment, the method of the invention is for inhibiting and/or preventing platelet recruitment by fibrin via GPVI, thereby treating a GPVI related condition.

In one embodiment, the method of the invention is for inhibiting and/or preventing GPVI-dependent thrombin production in response to fibrin, thereby treating a GPVI related condition.

In one embodiment, administering a protein as described hereinabove to a subject does not induce depletion of GPVI in vivo.

In one embodiment, administering a protein as described hereinabove to a subject does not induce a decrease in platelet count. Thus, in one embodiment, administering a protein as described hereinabove to a subject does not induce thrombocytopenia.

In one embodiment, administering a protein as described hereinabove to a subject does not induce an increase in bleeding time.

In one embodiment, the method of the invention comprises administering a therapeutically effective amount of the protein to the subject.

The present invention further relates to a method for enhancing the potency of a thrombolytic agent (preferably t-PA (including native t-PA and recombinant t-PA, as well as modified forms of t-PA that retain the enzymatic and/or fibrinolytic activity of native t-PA)) for treating a GPVI-related disease, wherein said method comprises administering a combination of said thrombolytic agent with a protein of the invention (preferably a therapeutically effective amount of the protein of the invention) to the subject.

In one embodiment, the method of the invention allows decreasing the dose of thrombolytic agent (preferably t-PA) to be administered to the subject.

EXAMPLES

The present invention is further illustrated by the following examples.

Example 1: Biologic Data in Non-Human Primates

Materials and Methods

Animals 28 cynomolgus monkeys free of any previous treatment were used in the study.

Treatment

First, increasing doses of ACT017 (1, 2, 4, 8 mg/kg) or its vehicle were intravenously administered over 15 minutes (n=4-8). At time 30 minutes and 2 hours after administration, blood was collected.

In a second experiment, ACT017 was administered to animals, by bolus injection or infusion. Three treatment groups were included in the study: ACT017 administered at 8 mg/kg by a bolus injection of 25 minutes (n=4), ACT017 administered at 8 mg/kg by an infusion of 1 hour (n=8), ACT017 administered at 2 mg/kg by a 15-min bolus injection followed by a 6 mg/kg infusion of 5 hours and 45 minutes (n=4). At different times, from 20 minutes to 24 hours after administration, blood was collected.

Analysis

Platelet aggregation: Platelet rich plasma (PRP) was obtained from monkeys after centrifugation (120×g; 15 min; 20° C.) and immediately used. The velocity and intensity of the aggregation were measured using the APACT® aggregometer and a collagen concentration of 2.5 mg. mL-1 (Horm collagen, Nycomed, DE) to the PRP containing various concentration of the Fab of the invention and continuously recorded. The intensity of platelet aggregation was measured as the percent increase in light transmission. The mean±SD are presented at the indicated time after the beginning of the injection.

Platelet count was measured in EDTA anticoagulated blood. The platelet count was determined in a Scil Vet abc automatic cell counter (Scil Animal Care Company, Holtzheim, France) set to monkey parameters.

The bleeding time was measured on vigil monkeys at the surface of the forearm, according to standard clinical procedure (Ivy's procedure) and using 0.5 cm Surgicutt™ bleeding time device.

GPVI expression: Blood samples were collected onto EDTA before injection and 30 minutes post injection of increasing doses of ACT017 or an equivalent volume of vehicle and were incubated with commercial FITC coupled anti-human GPVI monoclonal antibody (clone 1G5, Biocytex) that cross react with cynomolgus GPVI, and fluorescence was measured on a Beckman Coulter Gallios Flow cytometer.

Results

The effect of ACT017 administration was characterized in non-human primates. Eight cynomolgus monkeys were enrolled in the study.

Figure 1A:
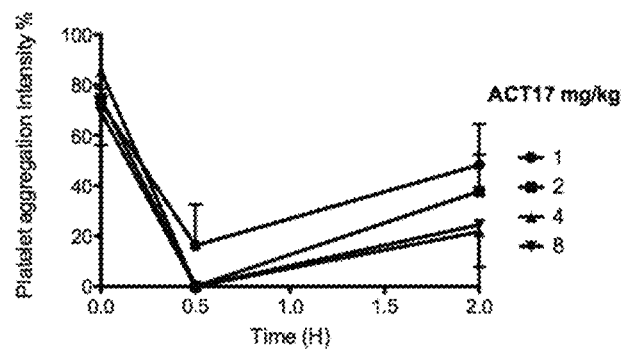
FIGS. 1A-1B are a combination of graphs showing the mean±SEM intensity (FIG. 1A) and velocity (FIG. 1B) of collagen-induced platelet aggregation measured 30 minutes and 2 hours after the end of a 15 minutes' infusion of increasing doses of ACT017 (1, 2, 4, 8 mg/kg) to cynomolgus monkeys (n=4).
Figure 1B:
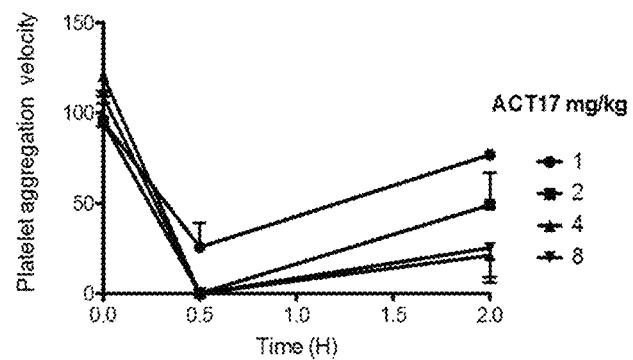
Figure 2:
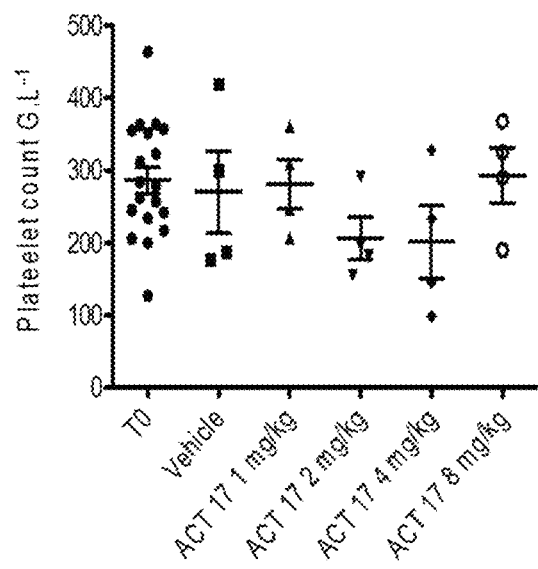
FIG. 2 is a graph showing the blood platelet count of cynomolgus measured before any treatment (T0) or 24 hours after the infusion of vehicle or ACT017 at increasing doses (1, 2, 4, 8 mg/kg).
Figure 3:
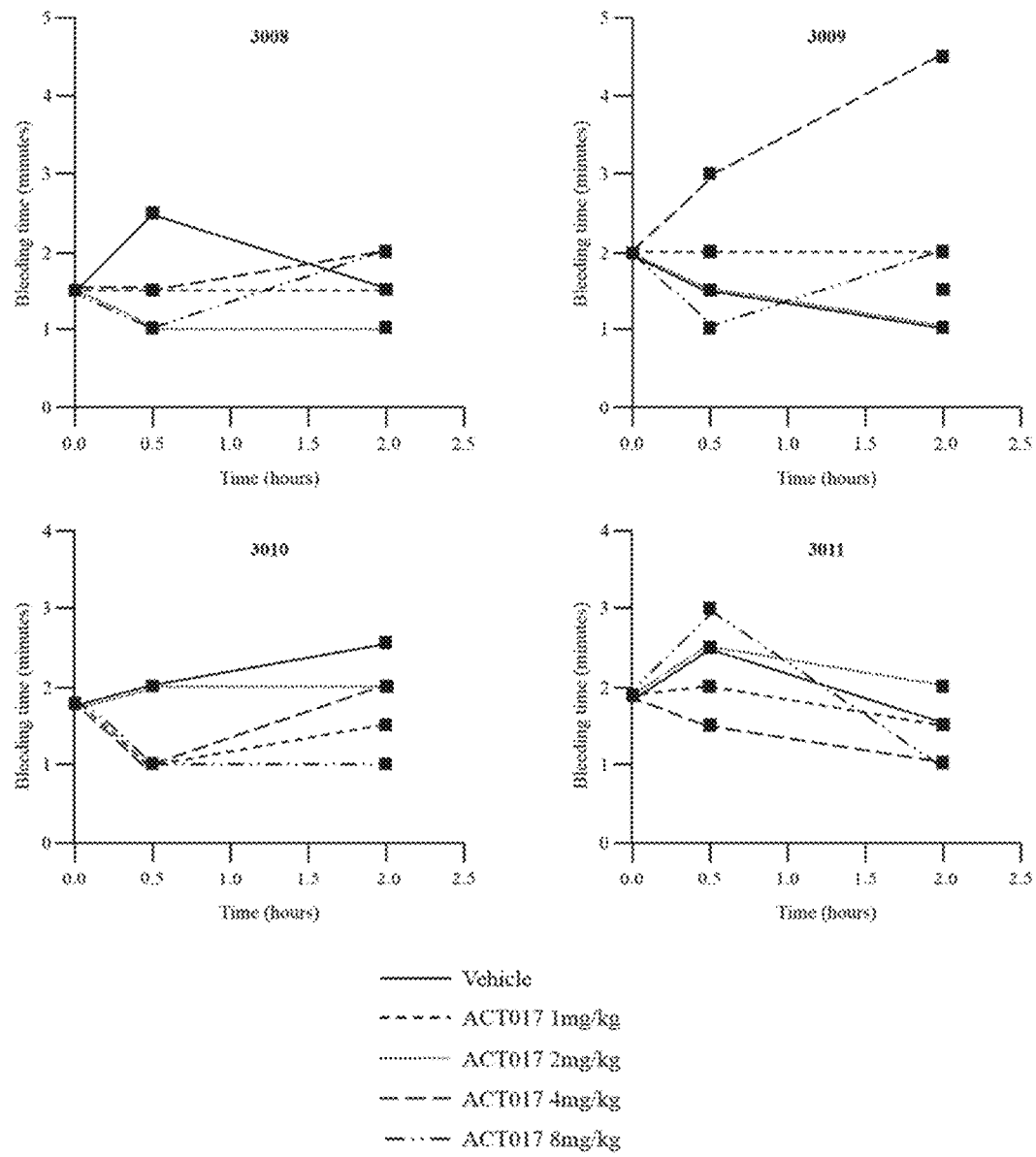
FIG. 3 is a combination of graphs showing the bleeding time measured in 4 subjects, before treatment (Time=0) and 30 min and 2 hours after the infusion of ACT017 (1, 2, 4, 8 mg/kg) or vehicle to cynomolgus monkeys.
Figure 4A:
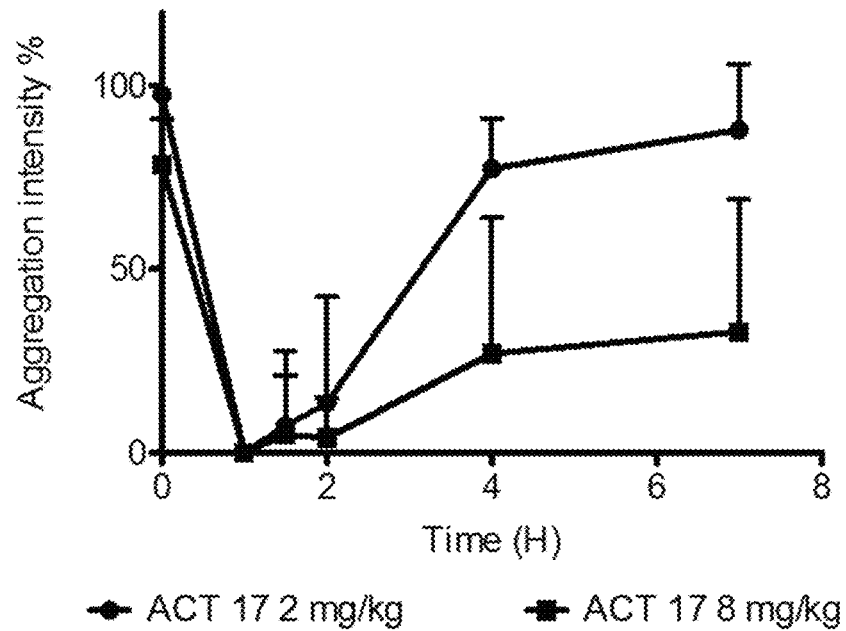
FIGS. 4A-4B are a combination of graphs showing the mean±SD intensity (FIG. 4A) and velocity (FIG. 4B) of collagen-induced platelet aggregation measured at different time after the beginning of a one-hour infusion of two doses of ACT017 (2 and 8 mg/kg) to cynomolgus monkeys (n=8).
Figure 4B:
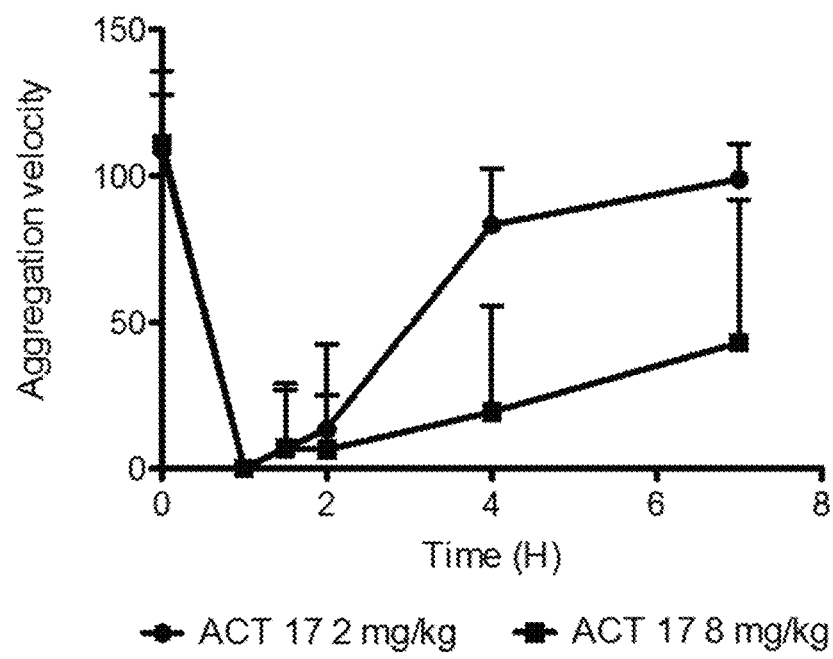
Figure 5:
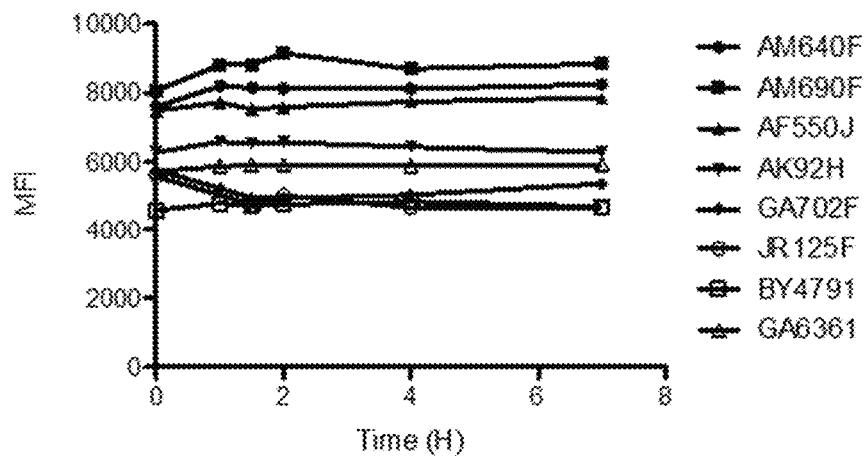
FIG. 5 is a graph showing the level of GPVI expression measured by flow cytometry on the platelets of cynomolgus monkeys (n=8) at different times after the beginning of a one-hour infusion of ACT017 at 2 mg/kg (MFI: Mean Fluorescence Intensity).

First, increasing doses of ACT017 (1, 2, 4, 8 mg/kg) were intravenously administrated over 15 minutes. At time 30 minutes and 2 hours after administration, blood was collected. Platelet aggregation was reversibly inhibited in a dose dependent manner (FIGS. 1A-1B). Increasing the dose from 1 to 2 and from 2 to 4 mg/kg increased the effect whereas 8 mg/kg had no additional effect as compared to 4 mg/kg. The platelet count measured 24 hours after the injection was not modified as compared to the values obtained before injection (FIG. 2). No significant increase in the bleeding time was observed after treatment with vehicle or 2, 4 or 8 mg/kg ACT017 (FIG. 3). Next, after a washing out period, the cynomolgus received ACT017 (2 or 8 mg/kg) administered as a one-hour perfusion. Platelet aggregation and GPVI expression were measured at different time after the beginning of the treatment: (1, 1.5, 2, 4 and 7 hours) (FIGS. 4 and 5). Collagen-induced platelet aggregation was reversibly inhibited and the duration of the effect was prolonged in cynomolgus treated with 8 mg/kg compared to 2 mg/kg (FIGS. 4A-4B). GPVI expression on platelets remained stable at the different time after the beginning of the treatment as compared to the pretreatment values (FIG. 5).

Together, these results confirm in non-human primates that administration of ACT017 efficiently and reversibly inhibits GPVI function without impact on the platelet count, on expression of GPVI at the platelet surface nor on bleeding time.

In addition, according to the preceding results, the inhibitory effect of ACT017 on platelet aggregation, after a 1-hour infusion appeared to be efficient during a limited period of time. Indeed, ACT017 induced a pronounced and stable inhibition on platelet aggregation only during 2 hours after the beginning of the administration, i.e. for at most 1 hour after the end of the 1-hour induction (see FIGS. 4A-4B). After 2 hours, even if the inhibition was prolonged at 8 mg/kg, ACT017 inhibitor effect regressed at all tested doses.

Figure 6:
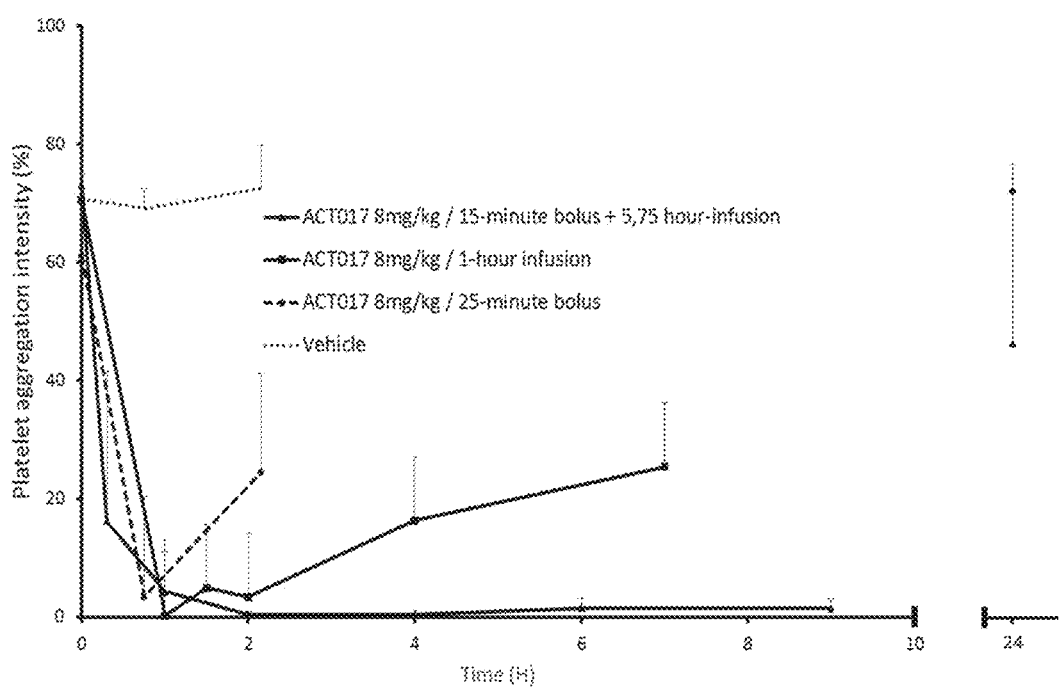
FIG. 6 is a graph showing the mean±SD intensity of collagen-induced platelet aggregation measured at different times (from 20 minutes to 24 hours) after the end of a 25-minute bolus injection of ACT017 8 mg/kg (n=4), a 1-hour infusion of ACT017 8 mg/kg (n=8), or a 15-minute bolus of ACT017 2 mg/kg followed by a 5-hour-45-minute infusion of ACT017 6 mg/kg to cynomolgus monkeys (n=4).

In a second experiment the effect of ACT017 at the dose of 8 mg/kg was further characterized on platelet aggregation after different administration times, including 1-hour and 6-hour administrations. Platelet aggregation was reversibly inhibited in a time dependent manner (FIG. 6).

A 25-minute bolus injection at 8 mg/kg induced a full inhibition of the collagen-induced platelet aggregation measured at 0.5 hour. At 2 hours, the inhibition of platelet aggregation regressed and the aggregation intensity returned to values of 24±34%. No effect of ACT017 can be observed at 24h.

A 1-hour infusion at 8 mg/kg resulted in a prolonged inhibition of collagen-induced platelet aggregation. However, the inhibition was total (<5%) for all animals only until 2 hours. At 4 hours and 7 hours after ACT017 administration, inhibition regressed and the overall mean intensity of aggregation was respectively 16±29% and 25±32%. Therefore, as for the 25-min administration, the inhibitory effect of ACT017 appears to be pronounced only during a short time after its 1-hour administration.

A 6-hour infusion at 8 mg/kg resulted in a profound inhibition of collagen-induced platelet aggregation lasting at least 9 hours. Indeed, during 9 hours after the beginning of the 6-hour infusion, platelet aggregation intensity was lower than 2%. Moreover, the possibility of a longer duration of the effect is not excluded since no analysis was performed between 9 hours and 24 hours. At 24 hours, the effect of ACT017 was close to be fully reversed for three out of the four animals and the mean intensity of aggregation reached 47±30%.

In conclusion, for the same dose of 8 mg/kg, a 6-hour infusion demonstrates a prolonged efficacy to inhibit collagen-induced platelet aggregation during at least 3 hours after the end of the administration.

Example 2: Study of ACTO17 Safety, Tolerability, Pharmacokinetic and Pharmacodynamic in Healthy Volunteers Materials and Methods The present study is a randomized, double blind, placebo-controlled ascending single dose study on the safety, tolerability, pharmacokinetics and pharmacodynamics of ACT017 in healthy volunteers.

Subjects

The subjects included in the study were healthy male or non-pregnant, non-breastfeeding female subject, aged between 30 and 60 year of age (inclusive) with a BMI≥18 kg/m2 and ≤30 kg/m2. A total of 48 subjects were enrolled in 6 ascending dose level cohorts with each cohort consisting of 8 subjects: 6 on active and 2 on placebo. Each cohort was divided into 2 sub-cohorts: one cohort dosed initially (1 active and 1 placebo) and the other cohort (5 active and 1 placebo) 48 hours thereafter.

On Day −1 of each dosing period, subjects were admitted to the research center and stay there until at least 48 hours' post-dose. A follow up visit was paid on Day 7. Subject were hospitalized from Day-1 until the morning of Day-3.

Treatment

Investigational drugs were 50 mL vial containing 500 mg of ACT017 and matching placebo solution. Treatments were given during an infusion of 6 hours.

Each dose was given as a 6-hour infusion, with a 15 minutes injection of a first bolus corresponding to about ¼ of the final dosage.

Cohort 1: Treatment A: 62.5 mg ACT017 (n=6), Treatment B: matching placebo (n=2).

Cohort 2: Treatment A: 125 mg ACT017 (n=6), Treatment B: matching placebo (n=2).

Cohort 3: Treatment A: 250 mg ACT017 (n=6), Treatment B: matching placebo (n=2).

Cohort 4: Treatment A: 500 mg ACT017 (n=6), Treatment B: matching placebo (n=2).

Cohort 5: Treatment A: 1000 mg ACT017 (n=6), Treatment B: matching placebo (n=2).

Cohort 6: Treatment A: 2000 mg ACT017 (n=6), Treatment B: matching placebo (n=2).

Analysis

Pharmacokinetic blood sampling for ACT017 implied 15 samples per subject.

Urine collection for ACT017 implied approximately 5 collection intervals per subject.

Safety and tolerability analysis included the following studies:

Adverse events: throughout the study;

Vital signs: frequently;

ECG (electrocardiogram): less frequent than vital signs;

Clinical laboratory including hematology: 2 times;

Coagulation parameters: 5 times;

Bleeding time: 4 times;
Platelet count: 7 times;
Platelet aggregation (collagen): 6 times;
Immunogenicity/ADA: 3 times.

Platelet aggregation: Platelet rich plasma (PRP) was obtained from healthy subjects having received the placebo or 500 mg of ACT017 intravenously with 25% of the dose administered in the first 15 min an 75% of the dose administered in the following 5 h 45 min, after centrifugation (120×g; 15 min; 20° C.) and immediately used. The intensity of the aggregation were measured using the APACT® aggregometer and a collagen concentration of 2.5 mg. mL-1 (Horm collagen, various concentration of the Fab of the invention and continuously recorded. The intensity of platelet aggregation was measured as the percent increase in light transmission.

Results

Figure 9:
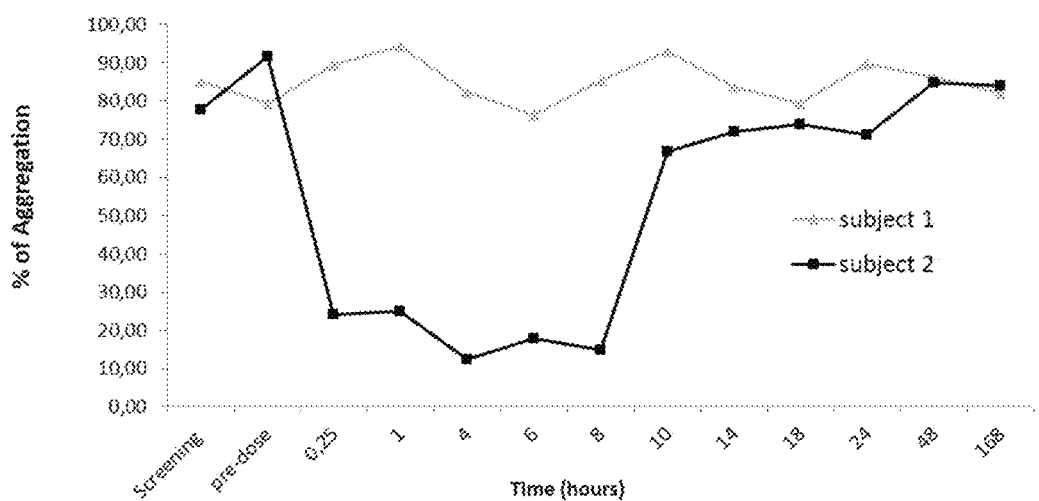
FIG. 9 is a graph showing the percentage of platelet aggregation measured with two healthy subjects of cohort 4 at different times (from 15 min to 168 hours). Subjects of cohort 4 were administered with 500 mg of ACT017 or of placebo. The "screening time" represents the measurement of the percentage of platelet aggregation one week or 24 hours before the administration of ACT017 or its matching placebo. The "pre-dose" represents the baseline measurement of the administration of the ACT017 or its matching placebo. In black is presented the graph for healthy subject 1 and in grey is presented the graph for healthy subject 2.

As shown by FIG. 9, the percentage of aggregation of platelets in subject 2 decreases by about 70% only 15 min after the beginning of the administrating in comparison with the baseline percentage and is maintained at about 10% for the next 8 hours, then it is increased again to reach about 70% of aggregation after 24 hours, and then returns to baseline 48 hours after administration. No effect is seen on platelet aggregation 168 hours after administration. The effect observed in subject 2 is thus reversible. In subject 1, the percentage of platelet aggregation seems unchanged during the 168 hours of the experience.

Example 3: Study of Epitopes Affinity of ACT017 on GPVI

The epitope of ACT017 on GPVI was previously identified by epitope mapping as being a conformational epitope comprising two regions on GPVI: amino acids 121-135 and amino acids 169-183 in SEQ ID NO: 13. In order to validate this epitope, a double mutant was constructed, comprising the following mutations: S125P, S126Q, G128R, Q133K, T136S, T171D, A172L and H174V and the affinity of this mutant for collagen and ACT017 was measured.

Materials and Methods

Soluble GPVI-Fc was produced as follows: a gene encoding the ectodomain of human GPVI from the first methionine to asparagine 269 fused to the human IgG1 Fc domain via the tripeptide GGR was synthesized after codon optimization. This gene was cloned into the pTT5 vector before being transfected into HEK 293-6E cells. Secreted GPVI-Fc was purified from the conditioned media of the cells by affinity chromatography using MAbselect matrix (GE Healthcare, 17519901) followed by a polishing chromatography on Nuvia™ HR-S cation exchange resin (BioRad, 156051).

Effect of Double Mutant on Binding of GPVI-Fc on Collagen—

Microtitration plates were coated with Collagen in PBS (20 μg/mL, 100 μL per well) overnight at 4° C.

Nonspecific binding sites were saturated with 200 μL of 1% BSA in PBS for 30 min. The plates were then incubated with increasing concentrations of wild-type or double mutant GPVI-Fc preparations (100 μL in PBS containing 0.1% BSA and 0.1% Tween 20) for 30 min. After 3 washing rounds plates were incubated with a peroxidase-coupled secondary human anti-Fc(ab) for 30 min. Finally, 100 μL of the substrate solution were added to each well for 4 min, and the colorimetric reaction stopped by 25 μL NaOH 3 M.

Effect of Double Mutant on Binding of ACT017 on GPVI-Fc—

Microtitration plates were coated with GPVI-Fc in PBS (20 μg/mL, 100 μL per well) overnight at 4° C. Nonspecific binding sites were saturated with 200 μL of 1% BSA in PBS for 30 min. The plates were then incubated with increasing concentrations of ACT017 preparations (100 μL in PBS containing 0.1% BSA and 0.1% Tween 20) for 30 min. After 3 washing rounds plates were incubated with a peroxidase-coupled secondary human anti-IgG for 30 min. Finally, 100 μL of the substrate solution were added to each well for 4 min, and the colorimetric reaction stopped by 25 μL NaOH 3 M.

Analysis

Absorbance at 450 nm is measured with Flustar Optima.

Results

Figure 7:
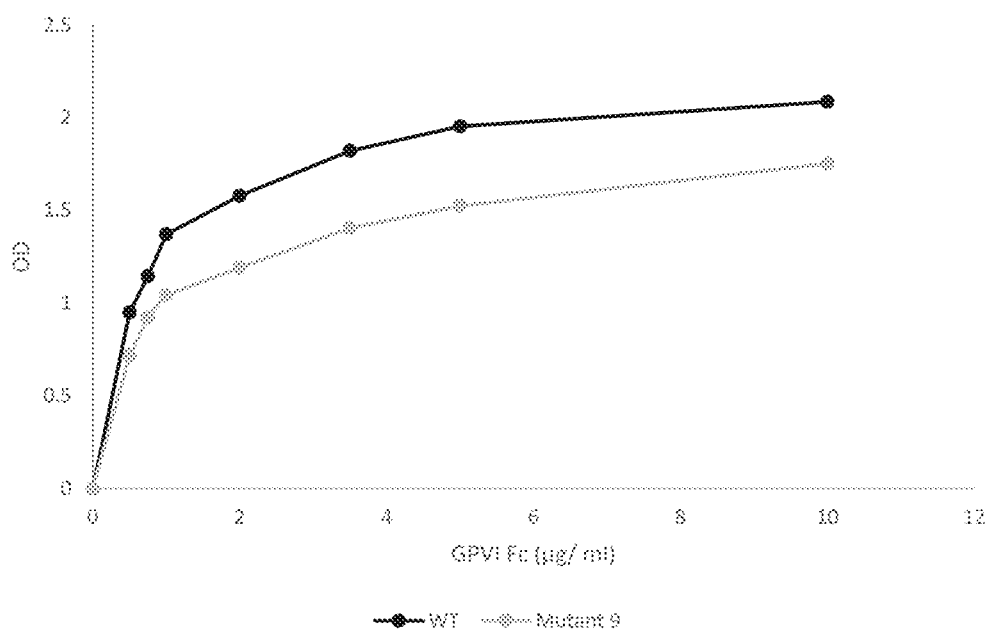
FIG. 7 is a graph showing the binding of wild-type GPVI-Fc (black graph) and GPVI double mutant (grey graph) on collagen.
Figure 8:
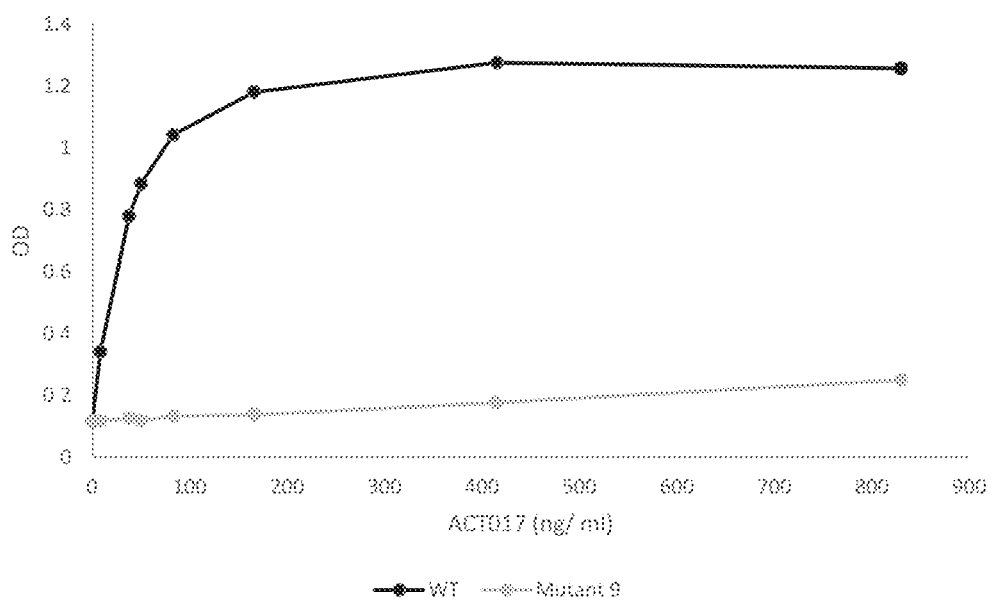
FIG. 8 is a graph showing the binding of ACT017 on wild-type GPVI-Fc (black graph) or on double mutant (grey graph).

As shown by FIG. 7, double mutant of GPVI-Fc is still capable to bind to collagen in a dose-dependent manner showing that the affinity of GPVI for collagen is mainly conserved in the presence of these mutations. However, as shown by FIG. 8, ACT017 is capable to bind wild-type GPVI-Fc, but not the double mutant, even at high concentrations. These results thus confirmed the position of the epitope of ACT017 on GPVI sequence.

The invention claimed is:

1. A method for treating a cardiovascular disease or event associated with inflammation and/or thrombosis in a subject in need thereof comprising administering an isolated humanized protein binding to human Glycoprotein VI (hGPVI), wherein said isolated humanized protein is administered for at least 2 hours, wherein said isolated humanized protein is a monovalent antibody fragment, wherein the variable region of the heavy chain of the antibody fragment comprises the following CDRs:

```
VH-CDR1:
                                (SEQ ID NO: 1)
GYTFTSYNMH;

VH-CDR2:
                                (SEQ ID NO: 2)
GIYPGNGDTSYNQKFQG;
and

VH-CDR3:
                                (SEQ ID NO: 3)
GTVVGDWYFDV;
``` and
the variable region of the light chain of the antibody fragment comprises the following CDRs:

```
VL-CDR1:
                                (SEQ ID NO: 4)
RSSQSLENSNGNTYLN;

VL-CDR2:
                                (SEQ ID NO: 5)
RVSNRFS;
and

VL-CDR3:
                                (SEQ ID NO: 6)
LQLTHVPWT.
```

2. The method according to claim 1, wherein said isolated humanized protein is administered during at least 4 to 6 hours.

3. The method according to claim 1, wherein the isolated humanized protein is injected.

4. The method according to claim 1, wherein the isolated humanized protein is administered by intravenous infusion.

5. The method according to claim 1, wherein a dose of humanized protein ranging from about 0.5 mg/kg to about 50 mg/kg is administered to the patient.

6. The method according to claim 1, wherein a dose of humanized protein ranging from about 1 mg/kg to about 32 mg/kg is administered to the patient.

7. The method according to claim 1, wherein a dose of humanized protein of about 8 mg/kg is administered to the patient.

8. The method according to claim 1, wherein a dose of humanized protein ranging from about 125 mg to about 2000 mg is administered to the patient.

9. The method according to claim 1, wherein a first bolus is administered.

10. The method according to claim 9, wherein the first bolus comprises about 10 to 50% of the total dosage of the isolated humanized protein to be administered.

11. The method according to claim 9, wherein said first bolus is administered in about 5 to 30 minutes.

12. The method according to claim 1, wherein said protein binds to a conformational epitope comprising:
at least one amino acid residue from amino acid residues 114 to 142 of hGPVI (SEQ ID NO: 13) or from a sequence sharing at least 60% of identity over amino acid residues 114 to 142 of hGPVI (SEQ ID NO: 13); and
at least one amino acid residue from amino acid residues 165 to 187 of hGPVI (SEQ ID NO: 13) or from a sequence sharing at least 60% of identity over amino acid residues 165 to 187 of hGPVI (SEQ ID NO: 13).

13. The method according to claim 12, wherein said conformational epitope comprises at least one amino acid residue from amino acid residues 121 to 135 or from 121 to 136 of hGPVI (SEQ ID NO: 13) or from a sequence sharing at least 60% of identity over amino acid residues 121 to 135 or from 121 to 136 of hGPVI (SEQ ID NO: 13); and at least one amino acid residue from amino acid residues 169 to 183 of hGPVI (SEQ ID NO: 13) or from a sequence sharing at least 60% of identity over amino acid residues 169 to 183 of hGPVI (SEQ ID NO: 13).

14. The method according to claim 1, wherein said protein has a KD for binding to hGPVI less than 15 nM, wherein said $K_D$ is measured by surface plasmon resonance using 960 to 1071 RU of soluble human GPVI and using PBS pH 7.4 as running buffer and wherein said isolated humanized protein does not induce a GPVI depletion phenotype in vivo.

15. The method according to claim 1, wherein said protein is a monovalent antibody fragment selected from the group consisting of a single chain antibody, a Fv, a Fab; and a unibody.

16. The method according to claim 1, wherein the amino acid sequence encoding the heavy chain variable region of the antibody fragment is SEQ ID NO:
7 and the amino acid sequence encoding the light variable region of the antibody fragment is SEQ ID NO: 8, or any sequence having an amino acid sequence that shares at least 60% of identity with said SEQ ID NO: 7 or 8.

17. The method according to claim 15, wherein the amino acid sequence encoding the heavy chain variable region of the antibody is SEQ ID NO: 7 and the amino acid sequence encoding the light variable region of the antibody is SEQ ID NO: 9, or any sequence having an amino acid sequence that shares at least 60% of identity with said SEQ ID NO: 7 or 9.

18. The method according to claim 1, wherein said cardiovascular disease or event associated with inflammation and/or thrombosis is selected from arterial and venous thrombosis, restenosis, acute coronary syndrome, cerebrovascular accidents due to atherosclerosis, critical limb ischemia, cerebral vascular diseases, ischemic stroke, venous thromboembolism diseases, thrombotic microangiopathies and vascular purpura.

19. The method according to claim 1, wherein said cardiovascular disease or event associated with inflammation and/or thrombosis is selected from coronary artery and cerebral artery diseases.

20. The method according to claim 1, wherein said cardiovascular disease or event associated with inflammation and/or thrombosis is selected from atherothrombosis, ischemic events, acute coronary artery syndrome, myocardial infarction, stroke, percutaneous coronary intervention, stenting thrombosis, ischemic restenosis, acute ischemia, chronic ischemia, diseases of the aorta and its branches, peripheral artery disease, venous thrombosis, acute phlebitis, pulmonary embolism, cancer-associated thrombosis, inflammatory thrombosis and thrombosis associated to infection.

* * * * *

SEQUENCE LISTING

```
<160> NUMBER OF SEQ ID NOS: 27

<210> SEQ ID NO 1
<211> LENGTH: 10
<212> TYPE: PRT
<213> ORGANISM: Artificial Sequence
<220> FEATURE:
<223> OTHER INFORMATION: VH-CDR1

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: VH-CDR2
```

```
<400> SEQUENCE: 2

Gly Ile Tyr Pro Gly Asn Gly Asp Thr Ser Tyr Asn Gln Lys Phe Gln
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: VH-CDR3

<400> SEQUENCE: 3

Gly Thr Val Val Gly Asp Trp Tyr Phe Asp Val
1               5                   10

<210> SEQ ID NO 4
<211> LENGTH: 16
<212> TYPE: PRT
<213> ORGANISM: Artificial Sequence
<220> FEATURE:
<223> OTHER INFORMATION: VL-CDR1

<400> SEQUENCE: 4

Arg Ser Ser Gln Ser Leu Glu Asn Ser Asn Gly Asn Thr Tyr Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: VL-CDR2

<400> SEQUENCE: 5

Arg Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL-CDR3

<400> SEQUENCE: 6

Leu Gln Leu Thr His Val Pro Trp Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Heavy chain variable region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45
```

Gly Gly Ile Tyr Pro Gly Asn Gly Asp Thr Ser Tyr Asn Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Thr Val Val Gly Asp Trp Tyr Phe Asp Val Trp Gly Gln
            100                 105                 110

Gly Thr Leu Val Thr Val Ser Ser
        115                 120

<210> SEQ ID NO 8
<211> LENGTH: 113
<212> TYPE: PRT
<213> ORGANISM: Artificial Sequence
<220> FEATURE:
<223> OTHER INFORMATION: Light chain variable region

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Leu Glu Asn Ser
            20                  25                  30

Asn Gly Asn Thr Tyr Leu Asn Trp Tyr Gln Gln Lys Pro Gly Lys Ala
            35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Leu Gln Leu
                85                  90                  95

Thr His Val Pro Trp Thr Phe Gly Gln Gly Thr Lys Val Glu Ile Thr
            100                 105                 110

Arg

<210> SEQ ID NO 9
<211> LENGTH: 113
<212> TYPE: PRT
<213> ORGANISM: Artificial Sequence
<220> FEATURE:
<223> OTHER INFORMATION: Light chain variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Ser Leu Glu Asn Ser
            20                  25                  30

Asn Gly Asn Thr Tyr Leu Asn Trp Tyr Gln Gln Lys Pro Gly Lys Ala
            35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Leu
                85                  90                  95

Thr His Val Pro Trp Thr Phe Gly Gln Gly Thr Lys Val Glu Ile Lys
                100                 105                 110

Arg

<210> SEQ ID NO 10
<211> LENGTH: 360
<212> TYPE: DNA
<213> ORGANISM: Artificial Sequence
<220> FEATURE:
<223> OTHER INFORMATION: Heavy chain variable region

<400> SEQUENCE: 10
caggttcagc tggttcagtc aggggctgag gtgaagaagc ctggagcctc agtgaaggtg      60
tcctgcaagg cttctggcta cacatttacc agttacaata tgcactgggt aagacaggct     120
cctggacagg gcctggaatg gatgggaggt atttatccag gaaatggtga tacttcctac     180
aatcagaagt tccagggccg agttactatg actcgggaca cttccacctc tacagtgtac     240
atggagctca gcagcctgag atctgaggac accgcggtct attactgtgc aagaggcacc     300
gtggtcggcg actggtactt cgatgtgtgg ggccaaggca ccctggtcac cgtgagcagt     360

<210> SEQ ID NO 11
<211> LENGTH: 339
<212> TYPE: DNA
<213> ORGANISM: Artificial Sequence
<220> FEATURE:
<223> OTHER INFORMATION: Light chain variable region

<400> SEQUENCE: 11
gacatccaga tgacccagag cccaagcagc ctgagcgcca gcgtgggtga cagagtgacc      60
atcacctgta aagtagtca gagccttgag aacagcaacg gaaacaccta cctgaattgg     120
taccagcaga gccaggtaa ggctccaaag ctgctgatct acagagtttc caaccgattc     180
tctggtgtgc caagcagatt cagcggtagc ggtagcggta ccgacttcac cttcaccatc     240
agcagcctcc agccagagga catcgccacc tactactgcc tccagctgac tcatgtccca     300
tggaccttcg gtcagggcac caaggtggag atcacccgg                            339

<210> SEQ ID NO 12
<211> LENGTH: 339
<212> TYPE: DNA
<213> ORGANISM: Artificial Sequence
<220> FEATURE:
<223> OTHER INFORMATION: Light chain variable region

<400> SEQUENCE: 12
gacatccaga tgacccagag cccaagcagc ctgagcgcca gcgtgggtga cagagtgacc      60
atcacctgta gtgccagtca gagccttgag aacagcaacg gaaacaccta cctgaattgg     120
taccagcaga gccaggtaa ggctccaaag ctgctgatct acagagtttc caaccgattc     180
tctggtgtgc caagcagatt cagcggtagc ggtagcggta ccgacttcac cctcaccatc     240
agcagcctcc agccagagga cttcgccacc tactactgcc tccagctgac tcatgtccca     300
tggaccttcg gtcagggcac caaggtggag atcaaacgc                            339

<210> SEQ ID NO 13
<211> LENGTH: 339
<212> TYPE: PRT
<213> ORGANISM: Homo sapiens

```
<400> SEQUENCE: 13

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser

<210> SEQ ID NO 14
<211> LENGTH: 321
<212> TYPE: DNA
<213> ORGANISM: Artificial Sequence
<220> FEATURE:
<223> OTHER INFORMATION: Heavy chain constant region
```

<400> SEQUENCE: 14

```
gcctccacca agggtccctc agtcttccca ctggcaccct cctccaagag cacctctggt      60
ggcacagctg ccctgggctg cctggtcaag gactacttcc cagaaccagt gactgtgtca     120
tggaactcag gcgccctgac cagcggcgtg cacaccttcc ctgctgtctt gcagtcctca     180
ggactctact ccctcagcag cgtggtgacc gtgccctcca gcagcttggg cacccagacc     240
tacatctgca acgtgaatca caagcccagc aacaccaagg tggacaagaa agtcgagcct     300
aagtcatgcg acaagactca c                                              321
```

<210> SEQ ID NO 15
<211> LENGTH: 318
<212> TYPE: DNA
<213> ORGANISM: Artificial Sequence
<220> FEATURE:
<223> OTHER INFORMATION: Light chain constant region

<400> SEQUENCE: 15

```
actgtggctg caccaagtgt gttcatcttc ccacctagcg atgagcagtt gaaatctgga      60
actgcctctg tcgtgtgcct cctgaacaac ttctacccac gggaggccaa ggtacagtgg     120
aaggtggata acgccctcca atccggtaac tcccaggaga gtgtcacaga gcaagatagc     180
aaggacagca cctacagcct cagcagcacc ctgactctga gcaaagcaga ctacgagaag     240
cacaaggtct acgcctgcga agtcacccat cagggcctga gttccctgt cacaaagagc     300 ttcaaccggg gagagtgt                                                  318
```

<210> SEQ ID NO 16
<211> LENGTH: 66
<212> TYPE: DNA
<213> ORGANISM: Artificial Sequence
<220> FEATURE:
<223> OTHER INFORMATION: Signal peptide

<400> SEQUENCE: 16

```
atggatatgc gtgtaccagc tcaactactt ggacttctat tgctttggct tcgtggtgct      60
agatgt                                                                66
```

<210> SEQ ID NO 17
<211> LENGTH: 57
<212> TYPE: DNA
<213> ORGANISM: Artificial Sequence
<220> FEATURE:
<223> OTHER INFORMATION: Signal peptide

<400> SEQUENCE: 17

```
atggactgga cttggagaat cctattcttg gttgctgcag ctacaggtgc tcattca        57
```

<210> SEQ ID NO 18
<211> LENGTH: 762
<212> TYPE: DNA
<213> ORGANISM: Artificial Sequence
<220> FEATURE:
<223> OTHER INFORMATION: Heavy chain

<400> SEQUENCE: 18

```
gcggccgcca ccatggactg gacttggaga atcctattct tggttgctgc agctacaggt      60
gctcattcac aggttcagct ggttcagtca ggggctgagg tgaagaagcc tggagcctca     120
gtgaaggtgt cctgcaaggc ttctggctac acatttacca gttacaatat gcactgggta     180
agacaggctc ctggacaggg cctggaatgg atgggaggta tttatccagg aaatggtgat     240
```

```
acttcctaca atcagaagtt ccagggccga gttactatga ctcgggacac ttccacctct      300
acagtgtaca tggagctcag cagcctgaga tctgaggaca ccgcggtcta ttactgtgca      360
agaggcaccg tggtcggcga ctggtacttc gatgtgtggg gccaaggcac cctggtcacc      420
gtgagcagtg cctccaccaa gggtccctca gtcttcccac tggcaccctc ctccaagagc      480
acctctggtg cacagctgc cctgggctgc ctggtcaagg actacttccc agaaccagtg      540
actgtgtcat ggaactcagg cgccctgacc agcggcgtgc acaccttccc tgctgtcttg      600
cagtcctcag gactctactc cctcagcagc gtggtgaccg tgcctccag cagcttgggc      660 acccagacct acatctgcaa cgtgaatcac aagcccagca acaccaaggt ggacaagaaa      720
gtcgagccta agtcatgcga caagactcac tgatgaggat cc                        762

<210> SEQ ID NO 19
<211> LENGTH: 742
<212> TYPE: DNA
<213> ORGANISM: Artificial Sequence
<220> FEATURE:
<223> OTHER INFORMATION: Light chain

<400> SEQUENCE: 19
gacgtcacca tggatatgcg tgtaccagct caactacttg gacttctatt gctttggctt       60
cgtggtgcta gatgtgacat ccagatgacc cagagcccaa gcagcctgag cgccagcgtg      120
ggtgacagag tgaccatcac ctgtagaagt agtcagagcc ttgagaacag caacggaaac      180
acctacctga attggtacca gcagaagcca ggtaaggctc caaagctgct gatctacaga      240
gtttccaacc gattctctgg tgtgccaagc agattcagcg gtagcggtag cggtaccgac      300
ttcaccttca ccatcagcag cctccagcca gaggacatcg ccacctacta ctgcctccag      360
ctgactcatg tccatggac cttcggtcag ggcaccaagg tggagatcac ccggactgtg      420
gctgcaccaa gtgtgttcat cttcccacct agcgatgagc agttgaaatc tggaactgcc      480
tctgtcgtgt gcctcctgaa caacttctac ccacgggagg ccaagtaca gtggaaggtg      540 gataacgccc tccaatccgg taactcccag agagtgtca cagagcaaga tagcaaggac      600
agcacctaca gcctcagcag cacccctgact ctgagcaaag cagactacga gaagcacaag      660
gtctacgcct gcgaagtcac ccatcagggc ctgagttccc ctgtcacaaa gagcttcaac      720
cggggagagt gttgatgata tc                                               742

<210> SEQ ID NO 20
<211> LENGTH: 742
<212> TYPE: DNA
<213> ORGANISM: Artificial Sequence
<220> FEATURE:
<223> OTHER INFORMATION: Light chain

<400> SEQUENCE: 20
gacgtcacca tggatatgcg tgtaccagct caactacttg gacttctatt gctttggctt       60
cgtggtgcta gatgtgacat ccagatgacc cagagcccaa gcagcctgag cgccagcgtg      120
ggtgacagag tgaccatcac ctgtagtgcc agtcagagcc ttgagaacag caacggaaac      180
acctacctga attggtacca gcagaagcca ggtaaggctc caaagctgct gatctacaga      240
gtttccaacc gattctctgg tgtgccaagc agattcagcg gtagcggtag cggtaccgac      300
ttcaccctca ccatcagcag cctccagcca gaggacttcg ccacctacta ctgcctccag      360
ctgactcatg tccatggac cttcggtcag ggcaccaagg tggagatcaa cgcactgtg       420 gctgcaccaa gtgtgttcat cttcccacct agcgatgagc agttgaaatc tggaactgcc      480
```

```
tctgtcgtgt gcctcctgaa caacttctac ccacgggagg ccaaggtaca gtggaaggtg    540
gataacgccc tccaatccgg taactcccag gagagtgtca cagagcaaga tagcaaggac    600
agcacctaca gcctcagcag caccctgact ctgagcaaag cagactacga gaagcacaag    660
gtctacgcct gcgaagtcac ccatcagggc ctgagttccc ctgtcacaaa gagcttcaac    720
cggggagagt gttgatgata tc                                             742
```

<210> SEQ ID NO 21
<211> LENGTH: 4
<212> TYPE: PRT
<213> ORGANISM: Artificial Sequence
<220> FEATURE:
<223> OTHER INFORMATION: CDR-L3 - Residues after
<220> FEATURE:
<221> NAME/KEY: SITE
<222> LOCATION: 3
<223> OTHER INFORMATION: X is any amino acid

<400> SEQUENCE: 21

Phe Gly Xaa Gly
1

<210> SEQ ID NO 22
<211> LENGTH: 4
<212> TYPE: PRT
<213> ORGANISM: Artificial Sequence
<220> FEATURE:
<223> OTHER INFORMATION: CDR-H1 - Residues before
<220> FEATURE:
<221> NAME/KEY: SITE
<222> LOCATION: 2
<223> OTHER INFORMATION: X is any amino acid
<220> FEATURE:
<221> NAME/KEY: SITE
<222> LOCATION: 3
<223> OTHER INFORMATION: X is any amino acid
<220> FEATURE:
<221> NAME/KEY: SITE
<222> LOCATION: 4
<223> OTHER INFORMATION: X is any amino acid

<400> SEQUENCE: 22

Cys Xaa Xaa Xaa
1

<210> SEQ ID NO 23
<211> LENGTH: 5
<212> TYPE: PRT
<213> ORGANISM: Artificial Sequence
<220> FEATURE:
<223> OTHER INFORMATION: CDR-H2 - Residues before

<400> SEQUENCE: 23

Leu Glu Trp Ile Gly
1               5

<210> SEQ ID NO 24
<211> LENGTH: 4
<212> TYPE: PRT
<213> ORGANISM: Artificial Sequence
<220> FEATURE:
<223> OTHER INFORMATION: CDR-H3 - Residues after
<220> FEATURE:
<221> NAME/KEY: SITE
<222> LOCATION: 3
<223> OTHER INFORMATION: X is any amino acid

```
<400> SEQUENCE: 24

Trp Gly Xaa Gly
1

<210> SEQ ID NO 25
<211> LENGTH: 527
<212> TYPE: PRT
<213> ORGANISM: Homo sapiens

<400> SEQUENCE: 25

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
            260                 265                 270

Gln Phe Arg Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Glu Gln Lys Phe
            340                 345                 350
```

-continued

Glu Val Glu Lys Tyr Ile Val His Lys Glu Phe Asp Asp Thr Tyr
355                 360                 365

Asp Asn Asp Ile Ala Leu Leu Gln Leu Lys Ser Asp Ser Ser Arg Cys
370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
        420                 425                 430

Val Arg Leu Tyr Pro Ser Ser Arg Cys Thr Ser Gln His Leu Leu Asn
    435                 440                 445

Arg Thr Val Thr Asp Asn Met Leu Cys Ala Gly Asp Thr Arg Ser Gly
450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
            485                 490                 495

Ser Trp Gly Leu Gly Cys Gly Gln Lys Asp Val Pro Gly Val Tyr Thr
        500                 505                 510

Lys Val Thr Asn Tyr Leu Asp Trp Ile Arg Asp Asn Met Arg Pro
    515                 520                 525

<210> SEQ ID NO 26
<211> LENGTH: 275
<212> TYPE: PRT
<213> ORGANISM: Homo sapiens

<400> SEQUENCE: 26

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

```
Ser Leu Thr Glu Ser Gly Ala Ser Cys Leu Pro Trp Asn Ser Met Ile
    195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
                260                 265                 270

Gln Phe Arg
        275

<210> SEQ ID NO 27
<211> LENGTH: 252
<212> TYPE: PRT
<213> ORGANISM: Homo sapiens

<400> SEQUENCE: 27

Ile Lys Gly Gly Leu Phe Ala Asp Ile Ala Ser His Pro Trp Gln Ala
1               5                   10                  15

Ala Ile Phe Ala Lys His Arg Arg Ser Pro Gly Glu Arg Phe Leu Cys
                20                  25                  30

Gly Gly Ile Leu Ile Ser Ser Cys Trp Ile Leu Ser Ala Ala His Cys
            35                  40                  45

Phe Gln Glu Arg Phe Pro Pro His His Leu Thr Val Ile Leu Gly Arg
    50                  55                  60

Thr Tyr Arg Val Val Pro Gly Glu Glu Glu Gln Lys Phe Glu Val Glu
65                  70                  75                  80

Lys Tyr Ile Val His Lys Glu Phe Asp Asp Asp Thr Tyr Asp Asn Asp
                85                  90                  95

Ile Ala Leu Leu Gln Leu Lys Ser Asp Ser Ser Arg Cys Ala Gln Glu
                100                 105                 110

Ser Ser Val Val Arg Thr Val Cys Leu Pro Pro Ala Asp Leu Gln Leu
            115                 120                 125

Pro Asp Trp Thr Glu Cys Glu Leu Ser Gly Tyr Gly Lys His Glu Ala
    130                 135                 140

Leu Ser Pro Phe Tyr Ser Glu Arg Leu Lys Glu Ala His Val Arg Leu
145                 150                 155                 160

Tyr Pro Ser Ser Arg Cys Thr Ser Gln His Leu Leu Asn Arg Thr Val
                165                 170                 175

Thr Asp Asn Met Leu Cys Ala Gly Asp Thr Arg Ser Gly Gly Pro Gln
                180                 185                 190

Ala Asn Leu His Asp Ala Cys Gln Gly Asp Ser Gly Gly Pro Leu Val
            195                 200                 205

Cys Leu Asn Asp Gly Arg Met Thr Leu Val Gly Ile Ile Ser Trp Gly
    210                 215                 220

Leu Gly Cys Gly Gln Lys Asp Val Pro Gly Val Tyr Thr Lys Val Thr
225                 230                 235                 240

Asn Tyr Leu Asp Trp Ile Arg Asp Asn Met Arg Pro
                245                 250
```